(12) United States Patent
Lu et al.

(10) Patent No.: US 9,939,453 B2
(45) Date of Patent: Apr. 10, 2018

(54) IMMATURE PLATELET ENUMERATION SYSTEMS AND METHODS

(71) Applicant: Beckman Coulter, Inc., Brea, CA (US)

(72) Inventors: Jiuliu Lu, Homestead, FL (US); Phaisit Chewputtanagul, Miami, FL (US); Christophe Godefroy, Miramar, FL (US); Patricio Vidal, Miami, FL (US); John Riley, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 715 days.

(21) Appl. No.: 14/142,369

(22) Filed: Dec. 27, 2013

(65) Prior Publication Data

US 2014/0186874 A1    Jul. 3, 2014

Related U.S. Application Data

(60) Provisional application No. 61/747,734, filed on Dec. 31, 2012.

(51) Int. Cl.
| | |
|---|---|
| *G01N 33/80* | (2006.01) |
| *G01N 15/02* | (2006.01) |
| *G01N 15/10* | (2006.01) |
| *G01N 15/12* | (2006.01) |
| *G01N 15/14* | (2006.01) |
| *G01N 15/00* | (2006.01) |

(52) U.S. Cl.
CPC .......... *G01N 33/80* (2013.01); *G01N 15/0211* (2013.01); *G01N 15/10* (2013.01); *G01N 15/12* (2013.01); *G01N 15/1459* (2013.01); *G01N 2015/0084* (2013.01)

(58) Field of Classification Search
None
See application file for complete search history.

(56) References Cited

U.S. PATENT DOCUMENTS

| | | | |
|---|---|---|---|
| 5,492,833 | A | 2/1996 | Rodriguez et al. |
| 5,616,501 | A | 4/1997 | Rodriguez et al. |
| 6,133,995 | A | 10/2000 | Kubota |
| 6,228,652 | B1 | 5/2001 | Rodriguez et al. |
| 6,246,786 | B1 | 6/2001 | Nishikiori et al. |
| 6,524,858 | B1 | 2/2003 | Zelmanovic et al. |

(Continued)

FOREIGN PATENT DOCUMENTS

| | | |
|---|---|---|
| CN | 1323395 A | 11/2001 |
| CN | 101358983 A | 2/2009 |

(Continued)

OTHER PUBLICATIONS

Beckman Coulter, "Advancements in Technology: CBC Methodology," Beckman Coulter, Inc., 2009, 2 pages, Brea, CA.

(Continued)

*Primary Examiner* — G. Steven Vanni
(74) *Attorney, Agent, or Firm* — Kilpatrick Townsend & Stockton LLP

(57) ABSTRACT

Embodiments of the present invention encompass automated systems and methods for analyzing immature platelet parameters in an individual based on a biological sample obtained from blood of the individual. Exemplary techniques involve correlating aspects of direct current (DC) impedance, radiofrequency (RF) conductivity, and/or light measurement data obtained from the biological sample with an evaluation of immature platelet conditions in the individual.

21 Claims, 19 Drawing Sheets

(56) References Cited

U.S. PATENT DOCUMENTS

| | | |
|---|---|---|
| 6,525,807 B1 | 2/2003 | Morikawa et al. |
| 2006/0210438 A1 | 9/2006 | Nagai et al. |
| 2008/0187951 A1 | 8/2008 | Nagai et al. |
| 2008/0241957 A1 | 10/2008 | Shibata et al. |
| 2009/0006003 A1 | 1/2009 | Hirayama et al. |
| 2009/0111118 A1 | 4/2009 | Mylvaganam et al. |
| 2011/0053210 A1 | 3/2011 | Matsumoto et al. |
| 2011/0053212 A1 | 3/2011 | Matsumoto et al. |

FOREIGN PATENT DOCUMENTS

| | | |
|---|---|---|
| EP | 1710558 A2 | 10/2006 |
| EP | 1785720 A2 | 5/2007 |
| EP | 1936352 A2 | 6/2008 |
| EP | 1953525 A2 | 8/2008 |
| WO | 1998002727 A1 | 1/1998 |
| WO | 2000023800 A1 | 4/2000 |
| WO | 00/49385 | 8/2000 |
| WO | 0058727 | 10/2000 |
| WO | 2004019031 A1 | 3/2004 |
| WO | 2004019047 A1 | 3/2004 |
| WO | 2004085989 A2 | 10/2004 |
| WO | 2007056621 A2 | 5/2007 |
| WO | 2007076188 A2 | 7/2007 |
| WO | 2008002745 A2 | 1/2008 |
| WO | 2000049385 A2 | 8/2008 |
| WO | 2009058876 A1 | 5/2009 |
| WO | 2010056740 A1 | 5/2010 |
| WO | 2011088314 A1 | 7/2011 |
| WO | 2011119163 A1 | 9/2011 |

OTHER PUBLICATIONS

Briggs, et al., "Continuing Developments With the Automated Platelet Count," Int. J. Lab Hematology, Jan. 18, 2007, 15 pages, London, UK.

Cremer, "The Immature Platelet Fraction (IPF) in Neonates," Sysmex Diagnostic Perspectives, 2011, vol. 1, 7 pages, Berlin, Germany.

Anonymous: "Coulter VCS reticulocyte method," Oct. 25, 1996, www.cyto.purdue.edu/cdroms/cyto2/6/coulter/ss000126.htm.

Kaplan, et al., "Validation of Low Platelet Counts from Coulter LH 750 and Coulter Gen-S Analyzers", Laboratory Hermatology, static. cjp.com/gems/labhem/7.4.Kaplan.PDF Aug. 27, 2001, pp. 198-203.

Rapi Stefano, et al. "Reticulocytes and reticulated platelets: Simultaneous measurement in whole blood by flow cytometry," Clinical Chemistry and Laboratory Medicine, Walter De Gruyter & Co, Berlin, New York, vol. 36, No. 4, Apr. 1, 1998, pp. 211-214.

International Search Report and Written Opinion of PCT/US2013/078135 dated Apr. 4, 2014, 18 pages.

CAP Today "Beckman Coulter, UniCel DxH 800 Hematology analzers", Nov. 2016, 3 pages.

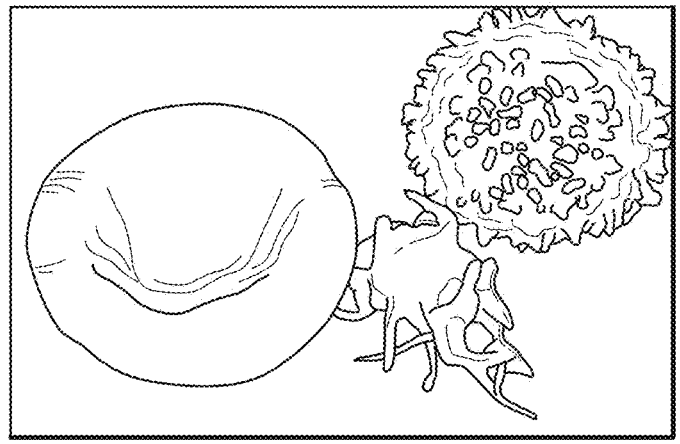
(RED BLOOD CELL, PLATELET, AND WHITE BLOOD CELL)
FIG.1A
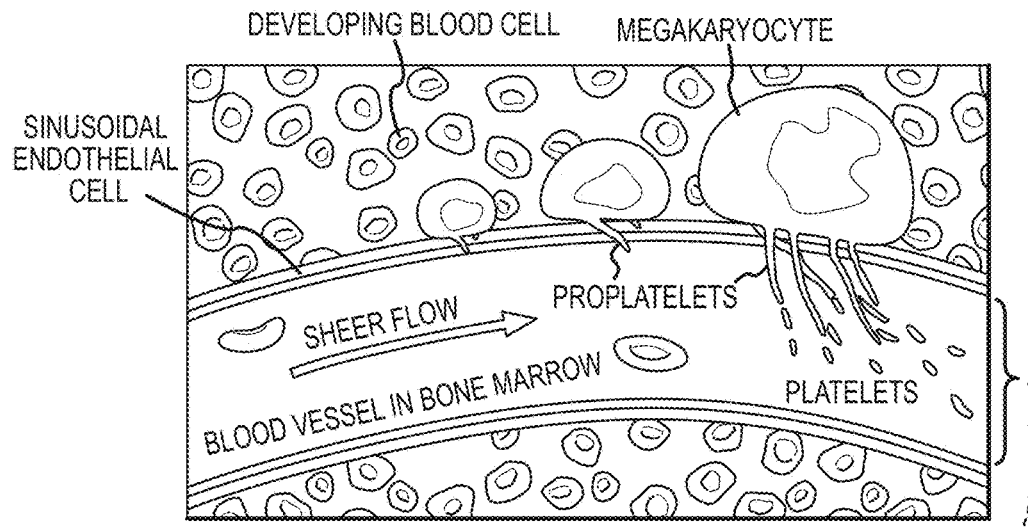
FIG.1B
$$\frac{\text{\# IMMATURE PLATELETS}}{\text{\# TOTAL PLATELETS (i.e. MATURE AND IMMATURE PLATELETS)}} \times 100\%$$
ANALYSIS OF IMMATURE PLATELET FRACTION (IPF)
FIG.1C

FIG. 7

GATED ON NOT DEBRIS EVENTS

GATED ON NOT WBC/NRBC EVENTS

GATED ON NOT PLATELET EVENTS (FIG.14)   GATED ON PLATELET EVENTS (FIG.15A-D)

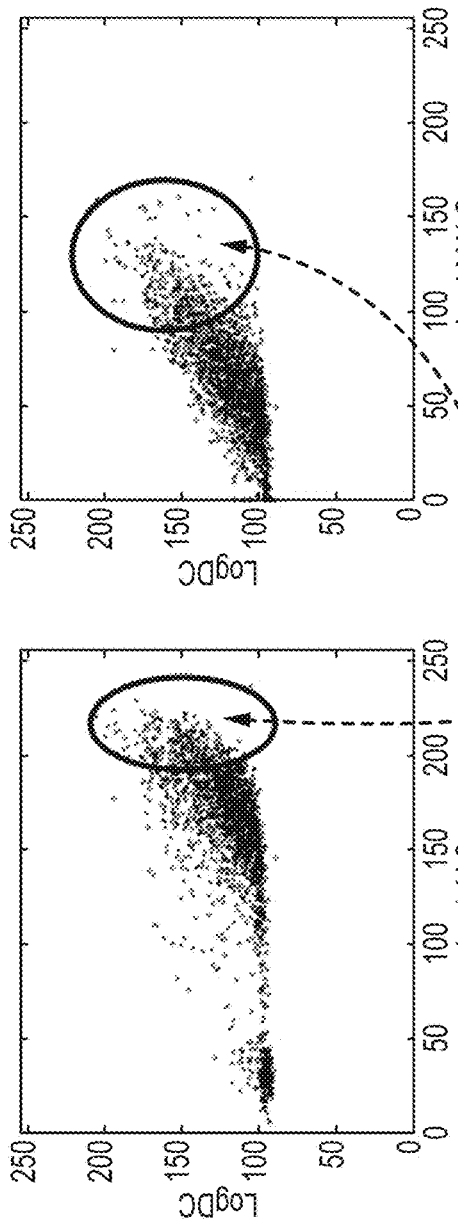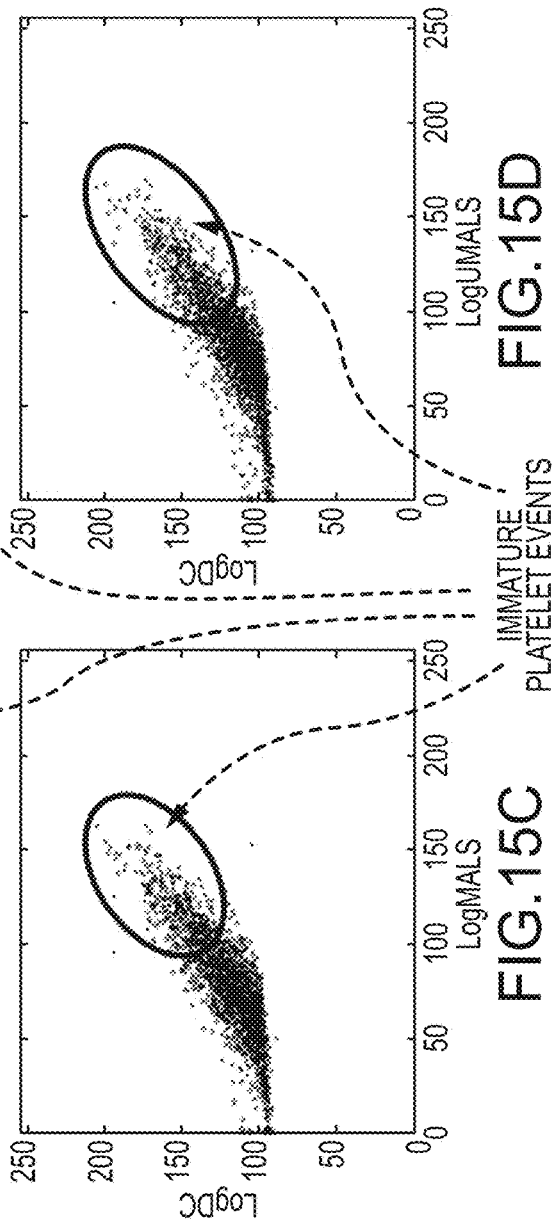

IMMATURE PLATELET ENUMERATION SYSTEMS AND METHODS

CROSS-REFERENCES TO RELATED APPLICATIONS

This application is a non-provisional of and claims the benefit of the filing date of U.S. Provisional Application No. 61/747,734, filed on Dec. 31, 2012, which is herein incorporated by reference in its entirety for all purposes.

BACKGROUND OF THE INVENTION

This invention relates to the field of medical diagnostics and more specifically to systems and methods for enumerating immature platelets in a biological sample from a patient.

Reticulated platelets (RP) or immature platelets (IP) are young platelets that contain increased levels of mRNA and rRNA compared to mature cells. When thrombocytes are released from the bone marrow into the peripheral circulation they contain residual RNA which is subsequently degraded as the cells circulate. Concurrently, the size of the immature platelets becomes smaller as they mature. These young reticulated platelets appear normally in the peripheral blood at low levels, up to 4.5% of total thrombocytes.

An increased proportion or count of reticulated platelets may indicate increased thrombopoiesis. The ability to detect increased platelet production has proven to be useful clinically in patients with thrombocytopenia. If these patients have elevated levels of reticulated platelets it implies that they may have a disease or condition resulting in peripheral destruction of platelets. In contrast, if their levels of reticulated platelets are depressed, it implies that they may have a disease or condition which impairs the ability of the bone marrow to make new platelets.

The determination or counting of reticulated platelets is useful for the evaluation of thrombopoietic disorders like thrombocytopenia, for monitoring course and treatment of Idiopathic Thrombocytopenic Purpura (ITP), thrombotic thrombocytopenic purpura (TTP), and disseminated intravascular coagulation (DIC). Immature platelet event parameters, such as IP count or IP percentage of total platelets, can also be used as an early indicator of marrow recovery in patients post-chemotherapy and stem cell transplant.

Immature platelets were first described in 1969 by direct visualization from peripheral blood. Immature platelets can also be measured by flow cytometry. In some instances, however, IP measurement using flow cytometry methods can be expensive, time consuming, and may require considerable expertise. Further, IP measurement using flow cytometry methods may lack adequate quality control and standardization Hence, although platelet analysis systems and methods are currently available and provide real benefits to patients in need thereof, many advances may still be made to provide improved devices and methods for assessing the status of platelets in an individual. Embodiments of the present invention provide solutions that address these problems, and hence provide answers to at least some of these outstanding needs.

BRIEF SUMMARY OF THE INVENTION

Embodiments of the present invention provide improved techniques for analyzing platelet conditions or parameters in an individual. Such techniques can employ various combinations of Complete Blood Cell Count (CBC) parameters in addition to Volume Conductivity Scatter (VCS) parameters, so as to provide reliable screening approaches that assess platelet conditions of patients or individuals in the general population. For example, diagnostic systems and methods can provide an early and accurate prediction as to whether an individual has normal or abnormal platelet counts or parameters. Such platelet analysis techniques may involve directly calculating certain immature platelet measures, such as immature platelet count, or percentage of immature platelets in a total platelet population.

Blood samples from patients who come under the care of a physician can be evaluated using a hematology system that is equipped to obtain multiple light angle detection parameters, such as Beckman Coulter's UniCel® DxH™ 800 Cellular Analysis System. By employing the techniques disclosed herein, hematopathologists and clinicians can better predict disease prognosis for each individual patient, assess the likelihood of future complications, and quickly and accurately tailor the therapy offered to patients.

The DxH 800 hematology analyzer is able to directly recognize morphologic features indicative of types of blood components such as white blood cells, red blood cells, and platelets. As discussed elsewhere herein, this technology simultaneously collects data on various parameters that are directly correlated to cellular morphology or certain cellular events. As cellular components are analyzed, they can be plotted in histograms with their position being defined by various parameters. For example, since immature platelets and mature platelets may have different features (e.g. size, amount of RNA), they can be plotted or segmented in different regions of the histogram, thus forming cell populations. The number of events in each population can be used to generate a count. Besides such counts, the mean and standard deviation values for the points of each of various morphologic parameters (volume, conductivity, and five angles of light scatter) can be calculated separately. As a result, a vast amount of data directly correlating to cellular events is generated. This information can be referred to as VCS data, and it can be viewed on the screen of the instrument, as well as automatically exported as an Excel file. Embodiments of the present invention may include evaluating a biological sample from an individual by obtaining a profile for the biological sample that involves VCS data, optionally in combination with CBC data, and assigning a platelet parameter such as an immature platelet count or fraction percentage indication to the biological sample based on the data. Certain embodiments may also include outputting the immature platelet count or fraction percentage indication. One or more of these steps may be performed by a hematology analyzer such as Beckman Coulter's UniCel® DxH™ 800 Cellular Analysis System.

Embodiments of the present invention provide quick and accurate platelet screening results. Using the approaches disclosed herein, it is possible to evaluate and predict a platelet condition in an individual, using information obtained from a multiparametric cellular analysis system. As disclosed herein, exemplary cellular analysis systems can simultaneously measure parameters such as volume, conductivity, and/or multiple angles of light scatter. Such systems provide a high degree of resolution and sensitivity for implementing cellular analysis techniques. In some instances, cellular analysis systems detect light scatter at three, four, five, or more angular ranges. Additionally, cellular analysis systems also can detect signals at an angle between 0° to about 1° from the incident light, which corresponds to a light extinction parameter known as axial light loss. As a non-limiting example, Beckman Coulter's UniCel® DxH™ 800 Cellular Analysis System provides light scatter detection data for multiple angles (e.g. between 0°-0.5° for AL2, about 5.1° for LALS, between 9°-19° for LMALS, and between 20°-43° for UMALS). These techniques allow for fast, accurate diagnosis and treatment of patients having abnormal platelet parameters, particularly in situations where more modern tests are not readily available.

Such hematology analysis instruments can evaluate more than 8,000 cells in a matter of seconds, and the morphologic features of cellular volume, cytoplasmic granularity, nuclear complexity, and internal density can be evaluated quantitatively. Numerical decision rules can be generated and used to implement strategies for predicting a platelet condition state or status in an individual. For example, a platelet condition state or status may be associated with an immature platelet count for the individual, or an immature platelet percentage for the individual. In some instances, the platelet condition or state may refer to a calculated immature platelet fraction for the individual.

Hence, embodiments of the present invention encompass systems and methods for the diagnosis or monitoring of platelet associated conditions using multiparametric models for disease classification. Patterns of morphological change can be analyzed by combining information from various measured parameters. Hence, embodiments of the present invention are well suited for use in analyzing reticulated platelet parameters for evaluating thrombopoietic disorders like thrombocytopenia, and for monitoring the course and treatment of Idiopathic Thrombocytopenic Purpura (ITP), thrombotic thrombocytopenic purpura (TTP), and disseminated intravascular coagulation (DIC). Reticulated platelet analysis systems and methods as disclosed herein can also be used to provide indicators of marrow recovery in patients post-chemotherapy and stem cell transplant.

In one aspect, embodiments of the present invention encompass automated systems and methods for estimating an immature platelet status in an individual based on a biological sample obtained from blood of the individual. Exemplary systems may include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone so as to measure light scattered by and transmitted through the irradiated cells of the biological sample. In some cases, the light detection assembly configured to measure a first propagated light from the irradiated cells within a first range of relative to the light beam axis, a second propagated light from the irradiated cells within a second range of angles relative to the light beam axis, the second range being different than the first range, and an axial light propagated from the irradiated cells along the beam axis. In certain embodiments, the system is configured to correlate a subset of DC impedance, the first propagated light, the second propagated light, and the axial light measurements from the cells of the biological sample with an estimation of an immature platelet status in the individual. According to some embodiments, the estimation of the immature platelet status of the individual includes an estimation of immature platelet count. According to some embodiments, the estimation of the immature platelet status of the individual includes an estimation of immature platelet percentage. In certain instances, the DC impedance measurement is obtained via a reticulocyte module, and the system is configured to correlate the DC impedance measurement with the estimation of the immature platelet status of the individual. Optionally, a light measurement of the subset can be obtained via a reticulocyte module, and the system can be configured to correlate the light measurement obtained via the reticulocyte module with the estimation of the immature platelet status of the individual. In some cases, a light measurement of the subset can be obtained via a reticulocyte module, the DC impedance measurement can also be obtained via the reticulocyte module, and the system can be configured to correlate the DC impedance measurement obtained via the reticulocyte module, the light measurement obtained via the reticulocyte module, and a platelet count obtained via a Complete Blood Cell Count module with the estimation of the immature platelet status of the individual. In some cases, the system includes the Complete Blood Cell Count module. In some cases, a light measurement of the subset which is obtained via the reticulocyte module can include a lower angle light scatter (LALS) measurement, a lower median angle light scatter (LMALS) measurement, an upper median angle light scatter (UMALS) measurement, or an axial light loss (ALL) measurement. In some cases, the biological sample is a blood sample of the individual.

In another aspect, embodiments of the present invention encompass systems and methods for estimating an immature platelet status in an individual based on a biological sample obtained from blood of the individual. Exemplary methods may include delivering a hydrodynamically focused stream of the biological sample toward a cell interrogation zone of an optical element, measuring, with an electrode assembly, current (DC) impedance of cells of the biological sample passing individually through the cell interrogation zone, irradiating, with an electromagnetic beam having an axis, cells of the biological sample individually passing through the cell interrogation zone, measuring, with a light detection assembly, a first propagated light from the irradiated cells within a first range of relative to the beam axis, measuring, with the light detection assembly, a second propagated light from the irradiated cells within a second range of angles relative to the beam axis, the second range being different than the first range, measuring, with the light detection assembly, axial light propagated from the irradiated cells along the beam axis, and correlating a subset of DC impedance, the first propagated light, the second propagated light, and the axial light measurements from the cells of the biological sample with an estimated immature platelet status of the individual.

In another aspect, embodiments of the present invention encompass methods of evaluating a biological sample from an individual that involve obtaining a current light propagation data profile for the biological sample, assigning an immature platelet status indication to the biological sample based on the current light propagation data profile, and outputting the assigned immature platelet status indication.

In another aspect, embodiments of the present invention encompass automated systems for estimating an immature platelet status of an individual based on a biological sample obtained from the individual. Exemplary systems include a conduit configured to receive and direct movement of the biological sample thorough an aperture, a light scatter and absorption measuring device configured to emit light through the biological sample as it moves through the aperture and collect data concerning scatter and absorption of the light, and a current measuring device configured to pass an electric current through the biological sample as it moves through the aperture and collect data concerning the electric current. In some cases, systems are configured to correlate the data concerning scatter and absorption of the light and the data concerning the electric current with an estimated immature platelet status of the individual.

In still another aspect, embodiments of the present invention encompass automated systems for estimating an immature platelet status of an individual based on a biological sample obtained from the individual. Exemplary systems include a transducer for obtaining light scatter data, light absorption data, and current data for the biological sample as the sample passes through an aperture, a processor, and a storage medium. In some instances, the storage medium has a computer application that, when executed by the processor, is configured to cause the system to use the light scatter data, the light absorption data, the current data, or a combination thereof, to determine an estimated immature platelet status of the individual, and to output from the processor information relating to the estimated immature platelet status.

In yet another aspect, embodiments of the present invention encompass automated systems for estimating an immature platelet status of an individual based on a biological sample obtained from the individual, where the systems include a transducer for obtaining current light propagation data for the biological sample as the sample passes through an aperture, a processor, and a storage medium. The storage medium may include a computer application that, when executed by the processor, is configured to cause the system to use the current light propagation data to determine an estimated immature platelet status of the individual, and to output from the processor information relating to the estimated immature platelet status.

In still another aspect, embodiments of the present invention include automated systems for identifying if an individual may have an abnormal immature platelet status based on a biological sample obtained from the individual. Exemplary systems may include a storage medium, a processor, and a transducer. The transducer can be configured to obtain light scatter data, light absorption data, and current data for the biological sample as the sample passes through an aperture. The storage medium may include a computer application that, when executed by the processor, is configured to cause the system to use a parameter, which is based on one or more measures of the light scatter data, light absorption data, or current data, to determine an estimated immature platelet status of the individual, and to output from the processor immature platelet information relating to the estimated immature platelet status of the individual.

In another aspect, embodiments of the present invention encompass systems and methods for evaluating a biological sample obtained from an individual. Exemplary methods may include passing the biological sample through an aperture of a particle analysis system, and obtaining light scatter data, light absorption data, and current data for the biological sample as the sample passes through the aperture. Exemplary methods may also include determining a current light propagation data profile for the biological sample based on the light scatter data, the light absorption data, the current data, or a combination thereof, and assigning an immature platelet status indication to the biological sample based on the current light propagation data profile. Exemplary methods may also include outputting the assigned immature platelet status indication.

In yet another aspect, embodiments of the present invention encompass automated methods for evaluating a biological sample from an individual. Exemplary methods include obtaining, using a particle analysis system, light scatter data, light absorption data, and current data for the biological sample as the sample passes through an aperture, and determining a current light propagation data profile for the biological sample based on assay results obtained from the particle analysis system. Exemplary methods may also include determining, using a computer system, an estimated immature platelet status for the individual according to a parameter, where the parameter is based on a current light propagation data measure of the current light propagation data profile. Exemplary methods may also include outputting the estimated immature platelet status.

In another aspect, embodiments of the present invention encompass automated systems for estimating an immature platelet status of an individual. Exemplary systems include a storage medium and a processor. The storage medium may include a computer application that, when executed by the processor, is configured to cause the system to access information concerning a biological sample of the individual. The information may include information relating at least in part to an axial light loss measurement of the sample, a light scatter measurement of the sample, a current measurement of the sample, or a combination of two or more thereof. The computer application may also, when executed by the processor, be configured to cause the system to use the information relating at least in part to the axial light loss measurement, the plurality of light scatter measurements, the current measurement, or the combination thereof, to determine an estimated immature platelet status of the individual. The computer application may also, when executed by the processor, be configured to cause the system to output from the processor information relating to the estimated immature platelet status. In some instances, the current measurement includes a low frequency current measurement of the sample. In some instances, the light scatter measurement includes a low angle light scatter measurement, a lower median angle light scatter measurement, an upper median angle light scatter measurement, or a combination of two or more thereof. In some cases, a system may include an electromagnetic beam source and a photosensor assembly. The photosensor assembly may be used to obtain the axial light loss measurement. In some instances, a system may include an electromagnetic beam source and a photosensor assembly, where the photosensor assembly is used to obtain the light scatter measurement. In some instances, a system may include an electromagnetic beam source and an electrode assembly, where the electrode assembly is used to obtain the current measurement.

In still another aspect, embodiments of the present invention encompass automated systems for estimating an immature platelet status of an individual. Exemplary systems may include a storage medium and a processor. The storage medium may include a computer application that, when executed by the processor, is configured to cause the system to access current light propagation data concerning a biological sample of the individual, to use the current light propagation data to determine an estimated immature platelet status of the individual, and to output from the processor information relating to the estimated immature platelet status. In some cases, the processor is configured to receive the current light propagation data as input. In some cases, the processor, the storage medium, or both, are incorporated within a hematology machine. In some cases, the hematology machine generates the current light propagation data. In some cases, the processor, the storage medium, or both, are incorporated within a computer, and the computer is in communication with a hematology machine. In some cases, the hematology machine generates the current light propagation data. In some cases, the processor, the storage medium, or both, are incorporated within a computer, and the computer is in remote communication with a hematology machine via a network. In some cases, the hematology machine generates the current light propagation data. In some cases, the current light propagation data includes an axial light loss measurement of the sample, a light scatter measurement of the sample, or a current measurement of the sample.

In another aspect, embodiments of the present invention encompass systems and methods for evaluating the physiological status of an individual. Exemplary systems may include a storage medium and a processor. The storage medium may include a computer application that, when executed by the processor, is configured to cause the system to access current light propagation data concerning a biological sample of the individual, and to use a parameter, which is based on a measure of the current light propagation data, to determine the physiological status of the individual. The determined physiological status can provide an indication whether the individual has a normal immature platelet status. The computer application may also, when executed by the processor, be configured to cause the system to output from the processor information relating to the physiological status of the individual.

In still yet another aspect, embodiments of the present invention encompass automated systems and methods for identifying if an individual may have an abnormal immature platelet status from hematology system data. Exemplary systems may include a storage medium and a processor. The storage medium may include a computer application that, when executed by the processor, is configured to cause the system to access hematology current light propagation data concerning a blood sample of the individual, and to use a parameter, which is based on a measure of the hematology current light propagation data, to determine an estimated immature platelet status of the individual. The computer application may also, when executed by the processor, be configured to cause the system to output from the processor immature platelet information relating to the estimated immature platelet status of the individual.

In a further aspect, embodiments of the present invention encompass automated systems and methods for evaluating a biological sample from an individual. Exemplary methods may include determining a current light propagation data profile for the biological sample based on assay results obtained from a particle analysis system analyzing the sample. Exemplary methods may also include determining, using a computer system, a physiological status for the individual according to a calculated parameter, where the calculated parameter is based on a function of a current light propagation data measure of the current light propagation data profile, and where the physiological status provides an indication whether the individual has a normal immature platelet status. Exemplary methods may also include outputting the physiological status.

In still yet a further aspect, embodiments of the present invention encompass systems and methods for determining a treatment regimen for a patient. Exemplary methods may include accessing a current light propagation data profile concerning a biological sample of the patient, and determining, using a computer system, an estimated immature platelet status for the patient based on the current light propagation data profile. Exemplary methods may also include determining the treatment regimen for the patient based on the estimated immature platelet status. In some instances, the estimated immature platelet status includes a positive indication for a platelet-related disease. In some instances, the estimated platelet status includes a negative indication for a platelet-related disease.

In another aspect, embodiments of the present invention encompass systems and methods for determining a treatment regimen for an individual. Exemplary methods may include accessing a current light propagation data profile concerning a biological sample of the individual, and determining, using a computer system, a physiological status for the individual according to a parameter, where the parameter is based on a current light propagation data measure of the current light propagation data profile, and where the physiological status corresponds to an estimated immature platelet status. Exemplary methods may also include determining the treatment regimen for the individual based on the a physiological status for the individual.

In still another aspect, embodiments of the present invention encompass automated systems and methods for estimating an immature platelet status of an individual based on a biological sample obtained from blood of the individual. Exemplary systems include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone. An exemplary light detection assembly may include a first sensor region disposed at a first location relative to the cell interrogation zone that detects a first propagated light, a second sensor region disposed at a second location relative to the cell interrogation zone that detects a second propagated light, and a third sensor region disposed at a third location relative to the cell interrogation zone that detects an axial propagated light. In some embodiments, the system is configured to correlate a subset of DC impedance, the first propagated light, the second propagated light, and the axial light measurements from the cells of the biological sample with an estimated immature platelet status of the individual.

In yet a further aspect, embodiments of the present invention encompass systems for estimating an immature platelet status in an individual based on a biological sample obtained from blood of the individual. Exemplary systems include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone so as to measure light scattered by and transmitted through the irradiated cells of the biological sample. An exemplary light detection assembly may be configured to measure a first propagated light from the irradiated cells within a first range of relative to the light beam axis, a second propagated light from the irradiated cells within a second range of angles relative to the light beam axis, the second range being different than the first range, and an axial light propagated from the irradiated cells along the beam axis. In certain embodiments, the system is configured to correlate a subset of Complete Blood Cell Count platelet measurements from the cells of the biological sample combined with the subset of DC impedance, the first propagated light, the second propagated light, and the axial light measurements with the estimation of the immature platelet status in the individual. In some instances, the light detection assembly includes a first sensor zone that measures the first propagated light, a second sensor zone that measures the second propagated light, and a third sensor zone that measures the axial propagated light. In some instances, the light detection assembly includes a first sensor that measures the first propagated light, a second sensor that measures the second propagated light, and a third sensor that measures the axial propagated light. In some instances, the system is configured to correlate a subset of Complete Blood Cell Count measurements from the cells of the biological sample combined with the subset of DC impedance, the first propagated light, the second propagated light, and the axial light measurements with the estimation of the immature platelet status in the individual. In some instances, the biological sample is a blood sample of the individual.

BRIEF DESCRIPTION OF THE DRAWINGS

FIGS. 1A to 1C illustrate aspects of immature platelet formation and analysis, according to embodiments of the present invention.

FIG. 7 depicts an exemplary screen shot of a differential count screen, according to embodiments of the present invention.

FIGS. 15A to 15D depict aspects of a gating technique according to embodiments of the present invention.

DETAILED DESCRIPTION OF THE INVENTION

Figure 2:
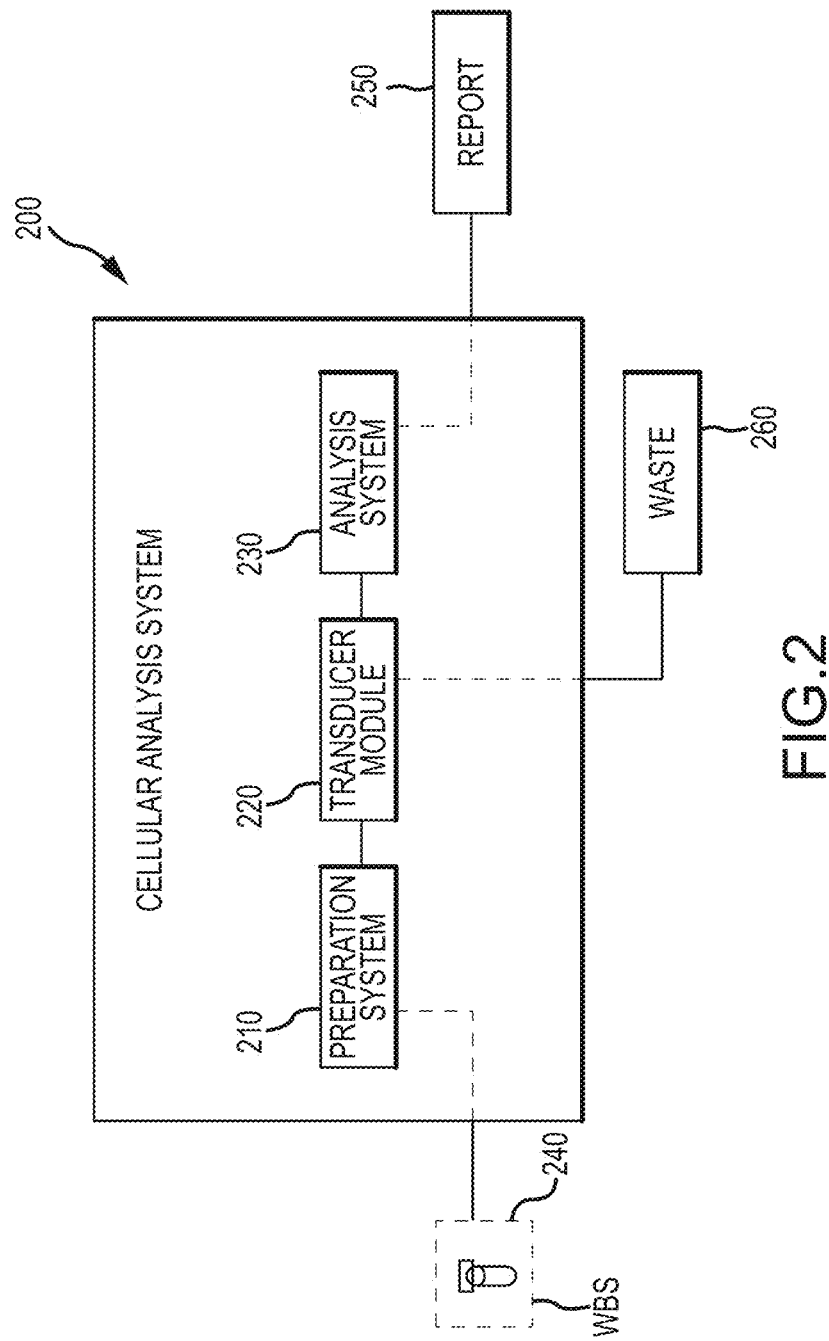
FIG. 2 schematically depicts aspects of a cellular analysis system, according to embodiments of the present invention.

For the purposes of explanation, and in brief overview, embodiments of the present invention encompass systems and methods which involve the use a reticulocyte module in a hematological analyzer for the enumeration of immature platelet fractions. An exemplary hematological cell analyzer may include a light source that produces a narrow directed beam of light toward a window in a flow cell. In various non-limiting embodiments, the light source is a laser or a laser diode, and a carrier fluid carries individual cells from a blood sample through the flow cell thereby allowing each individual cell to interact with the light beam. A plurality of photosensors located adjacent the flow cell can be used to record the intensity of light scattered at various angles by cells passing through the flow cell. In certain embodiments, one photosensor is positioned directly in the path of the light beam, and three groups of photosensors are positioned to collect light scattered by the cells in predetermined angular ranges as measured from the path of the light beam. Signals from these detectors can be transmitted to a processor, digitized, analyzed and the results displayed.

According to some embodiments, a reticulocyte module can be used to analyze blood cells of a biological sample obtained from an individual. In certain embodiments, cells of a blood sample are incubated with a first reagent to selectively stain the ribonucleic acid of the immature platelets. In one embodiment the stain New Methylene Blue (NMB) is used.

Hence, described herein are hematology systems and methods configured to assess platelet status conditions of an individual, based on a biological sample obtained from the individual. FIG. 1A provides a scanning electron micrograph of blood cells, including a red blood cell (left, human erythrocyte), platelet (middle, thrombocyte), and white blood cell (right, leukocyte). Each of these three blood cell types are generated in the bone marrow. FIG. 1B provides a schematic illustration of the platelet formation process within the human body. As shown here, platelets are derived from megakaryocytes, which are large cells in the bone marrow. Megakaryocytes extend into small vessels of the bone marrow, and fragments of the megakaryocyte cytoplasm are released to form immature platelets. The platelets mature following release into the blood circulation. Platelets have a life cycle of about 7-10 days, and platelet formation and replacement is a continuous cycle. Platelets play an important role in hemostasis and clot formation. As depicted in FIG. 1C, various platelet parameters can be evaluated to assess the platelet status of an individual. For example, exemplary evaluation techniques may involve obtaining a count of immature platelets in the blood, or the percentage of total counted platelets which are immature. The hematology systems and methods discussed herein can assess whether an individual is presenting with normal or abnormal immature platelet parameters based on data related to certain impedance, conductivity, and angular light propagation measurements of a biological sample of the individual.

Cellular analysis systems that detect light scatter at multiple angles can be used to analyze a biological sample (e.g. a blood sample) and output a predicted immature platelet status of an individual. Exemplary systems are equipped with sensor assemblies that obtain light scatter data for three or more angular ranges, in addition to light transmission data associated with an extinction or axial light loss measure, and thus provide accurate, sensitive, and high resolution results without requiring the use of certain dye, antibody, or fluorescence techniques. In one instance, a hematology analyzer such as a DxH 800 Hematology Analyzer (Beckman Coulter, Brea, Calif., USA) is configured to analyze a biological sample (e.g. a blood sample) based on multiple light scatter angles and output a predicted immature platelet status of an individual. The DxH 800 includes various channel processing modules that are configured to recognize the morphologic features indicative of cellular components within the blood. For example, the DxH includes a reticulocyte channel processing module that is configured to analyze certain blood cell components. The DxH 800 is configured to generate a significant amount of data based on analysis of the sample, this such data, which is described in detail herein, can be referred to as CBC data or VCS data.

In some embodiments, VCS data is based on the determination of different parameters for each cell of the sample analyzed, such parameters correlating to each cell's morphology. Specifically, a volume parameter corresponding to the cell size can be measured directly by impedance. Further, a conductivity parameter corresponding to the internal cellular density can be measured directly by the conduction of radio frequency waves across the cell. What is more, five different angles (or ranges of angles) of light scatter corresponding to cytoplasmic granularity and nuclear complexity, for example, can be measured with various light detection mechanisms.

FIG. 2 schematically depicts a cellular analysis system 200. As shown here, system 200 includes a preparation system 210, a transducer module 220, and an analysis system 230. While system 200 is herein described at a very high level, with reference to the three core system blocks (210, 220, and 230), the skilled artisan would readily understand that system 200 includes many other system components such as central control processor(s), display system(s), fluidic system(s), temperature control system(s), user-safety control system(s), and the like. In operation, a whole blood sample (WBS) 240 can be presented to the system 200 for analysis. In some instances, WBS 240 is aspirated into system 200. Exemplary aspiration techniques are known to the skilled artisan. After aspiration, WBS 240 can be delivered to a preparation system 210. Preparation system 210 receives WBS 240 and can perform operations involved with preparing WBS 240 for further measurement and analysis. For example, preparation system 210 may separate WBS 240 into predefined aliquots for presentation to transducer module 220. Preparation system 210 may also include mixing chambers so that appropriate reagents may be added to the aliquots. For example, where an aliquot is to be tested for differentiation of white blood cell subset populations, a lysing reagent (e.g. ERYTHROLYSE, a red blood cell lysing buffer) may be added to the aliquot to break up and remove the RBCs. Preparation system 210 may also include temperature control components to control the temperature of the reagents and/or mixing chambers. Appropriate temperature controls can improve the consistency of the operations of preparation system 210.

In some instances, predefined aliquots can be transferred from preparation system 210 to transducer module 220. As described in further detail below, transducer module 220 can perform direct current (DC) impedance, radiofrequency (RF) conductivity, light transmission, and/or light scatter measurements of cells from the WBS passing individually therethrough. Measured DC impedance, RF conductivity, and light propagation (e.g. light transmission, light scatter) parameters can be provided or transmitted to analysis system 230 for data processing. In some instances, analysis system 230 may include computer processing features and/or one or more modules or components such as those described herein with reference to the system depicted in FIG. 6 and described further below, which can evaluate the measured parameters, identify and enumerate the blood cellular constituents, and correlate a subset of data characterizing elements of the WBS with an immature platelet status of the individual. As shown here, cellular analysis system 200 may generate or output a report 250 containing the predicted immature platelet status and/or a prescribed treatment regimen for the individual. In some instances, excess biological sample from transducer module 220 can be directed to an external (or alternatively internal) waste system 260.

Treatment regimens may involve administration of one or more medications or therapeutic agents to an individual for the purposes of addressing the patient's condition. Any of a variety of therapeutic modalities can be used for treating an individual identified as having an abnormal immature platelet count or percentage as discussed herein.

Figure 3:
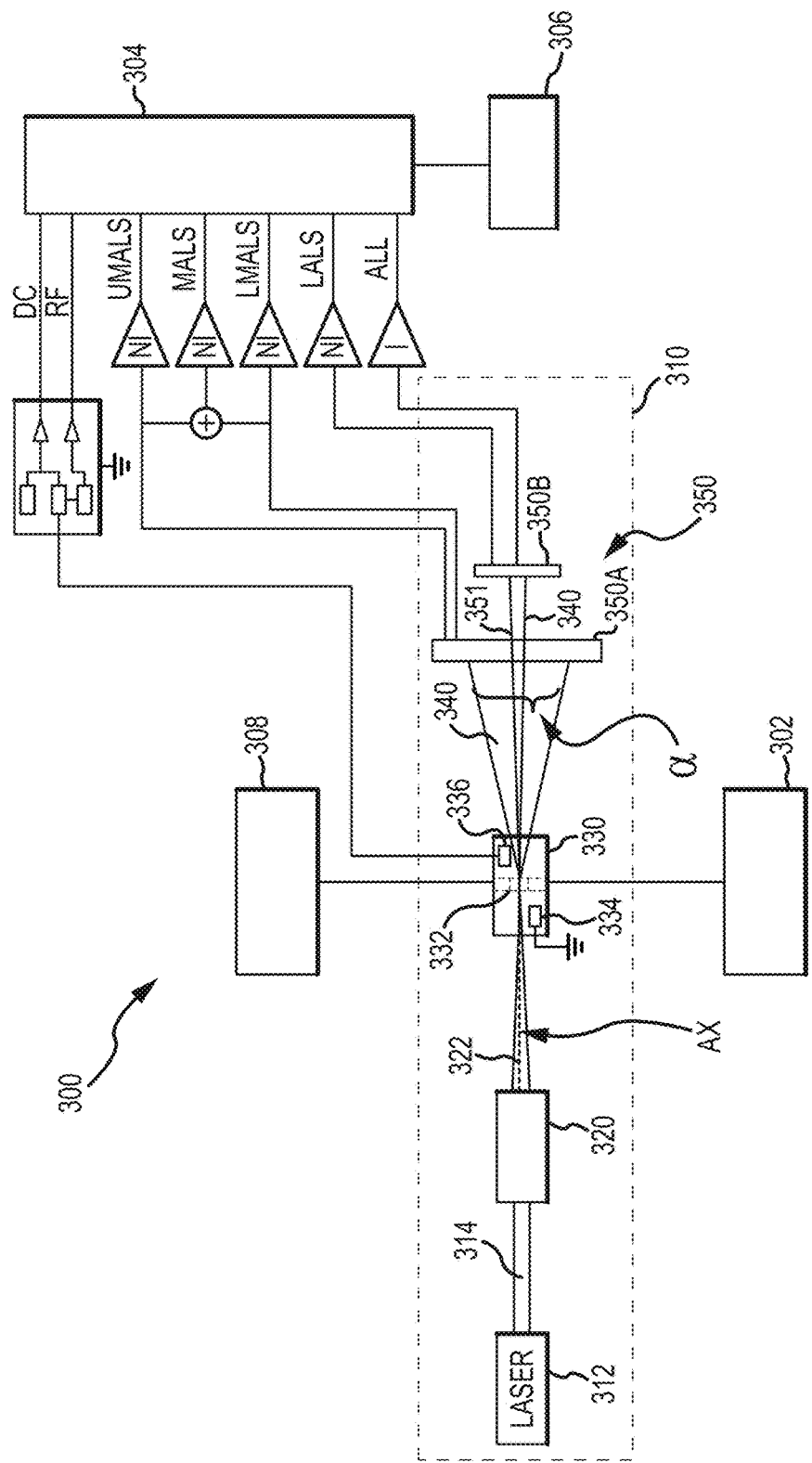
FIG. 3 provides a system block diagram illustrating aspects of a cellular analysis system according to embodiments of the present invention.

FIG. 3 illustrates in more detail a transducer module and associated components in more detail. As shown here, system 300 includes a transducer module 310 having a light or irradiation source such as a laser 310 emitting a beam 314. The laser 312 can be, for example, a 635 nm, 5 mW, solid-state laser. In some instances, system 300 may include a focus-alignment system 320 that adjusts beam 314 such that a resulting beam 322 is focused and positioned at a cell interrogation zone 332 of a flow cell 330. In some instances, flow cell 330 receives a sample aliquot from a preparation system 302. As described elsewhere herein, various fluidic mechanisms and techniques can be employed for hydrodynamic focusing of the sample aliquot within flow cell 330.

In some instances, the aliquot generally flows through the cell interrogation zone 332 such that its constituents pass through the cell interrogation zone 332 one at a time. In some cases, a system 300 may include a cell interrogation zone or other feature of a transducer module or blood analysis instrument such as those described in U.S. Pat. Nos. 5,125,737; 6,228,652; 7,390,662; 8,094,299; and 8,189,187, the contents of which are incorporated herein by references. For example, a cell interrogation zone 332 may be defined by a square transverse cross-section measuring approximately 50×50 microns, and having a length (measured in the direction of flow) of approximately 65 microns. Flow cell 330 may include an electrode assembly having first and second electrodes 334, 336 for performing DC impedance and RF conductivity measurements of the cells passing through cell interrogation zone 332. Signals from electrodes 334, 336 can be transmitted to analysis system 304. The electrode assembly can analyze volume and conductivity characteristics of the cells using low-frequency current and high-frequency current, respectively. For example, low-frequency DC impedance measurements can be used to analyze the volume of each individual cell passing through the cell interrogation zone. Relatedly, high-frequency RF current measurements can be used to determine the conductivity of cells passing through the cell interrogation zone. Because cell walls act as conductors to high frequency current, the high frequency current can be used to detect differences in the insulating properties of the cell components, as the current passes through the cell walls and through each cell interior. High frequency current can be used to characterize nuclear and granular constituents and the chemical composition of the cell interior.

Incoming beam 322 travels along beam axis AX and irradiates the cells passing through cell interrogation zone 332, resulting in light propagation within an angular range α (e.g. scatter, transmission) emanating from the zone 332. Exemplary systems are equipped with sensor assemblies that can detect light within three, four, five, or more angular ranges within the angular range α, including light associated with an extinction or axial light loss measure as described elsewhere herein. As shown here, light propagation 340 can be detected by a light detection assembly 350, optionally having a light scatter detector unit 350A and a light scatter and transmission detector unit 350B. In some instances, light scatter detector unit 350A includes a photoactive region or sensor zone for detecting and measuring upper median angle light scatter (UMALS), for example light that is scattered or otherwise propagated at angles relative to a light beam axis within a range from about 20 to about 42 degrees. In some instances, UMALS corresponds to light propagated within an angular range from between about 20 to about 43 degrees, relative to the incoming beam axis which irradiates cells flowing through the interrogation zone. Light scatter detector unit 350A may also include a photoactive region or sensor zone for detecting and measuring lower median angle light scatter (LMALS), for example light that is scattered or otherwise propagated at angles relative to a light beam axis within a range from about 10 to about 20 degrees. In some instances, LMALS corresponds to light propagated within an angular range from between about 9 to about 19 degrees, relative to the incoming beam axis which irradiates cells flowing through the interrogation zone.

A combination of UMALS and LMALS is defined as median angle light scatter (MALS), which is light scatter or propagation at angles between about 9 degrees and about 43 degrees relative to the incoming beam axis which irradiates cells flowing through the interrogation zone.

As shown in FIG. 3, the light scatter detector unit 350A may include an opening 351 that allows low angle light scatter or propagation 340 to pass beyond light scatter detector unit 350A and thereby reach and be detected by light scatter and transmission detector unit 350B. According to some embodiments, light scatter and transmission detector unit 350B may include a photoactive region or sensor zone for detecting and measuring lower angle light scatter (LALS), for example light that is scattered or propagated at angles relative to an irradiating light beam axis of about 5.1 degrees. In some instances, LALS corresponds to light propagated at an angle of less than about 9 degrees, relative to the incoming beam axis which irradiates cells flowing through the interrogation zone. In some instances, LALS corresponds to light propagated at an angle of less than about 10 degrees, relative to the incoming beam axis which irradiates cells flowing through the interrogation zone. In some instances, LALS corresponds to light propagated at an angle of about 1.9 degrees±0.5 degrees, relative to the incoming beam axis which irradiates cells flowing through the interrogation zone. In some instances, LALS corresponds to light propagated at an angle of about 3.0 degrees±0.5 degrees, relative to the incoming beam axis which irradiates cells flowing through the interrogation zone. In some instances, LALS corresponds to light propagated at an angle of about 3.7 degrees±0.5 degrees, relative to the incoming beam axis which irradiates cells flowing through the interrogation zone. In some instances, LALS corresponds to light propagated at an angle of about 5.1 degrees±0.5 degrees, relative to the incoming beam axis which irradiates cells flowing through the interrogation zone. In some instances, LALS corresponds to light propagated at an angle of about 7.0 degrees±0.5 degrees, relative to the incoming beam axis which irradiates cells flowing through the interrogation zone.

According to some embodiments, light scatter and transmission detector unit 350B may include a photoactive region or sensor zone for detecting and measuring light transmitted axially through the cells, or propagated from the irradiated cells, at an angle of 0 degrees relative to the incoming light beam axis. In some cases, the photoactive region or sensor zone may detect and measure light propagated axially from cells at angles of less than about 1 degree relative to the incoming light beam axis. In some cases, the photoactive region or sensor zone may detect and measure light propagated axially from cells at angles of less than about 0.5 degrees relative to the incoming light beam axis less. Such axially transmitted or propagated light measurements correspond to axial light loss (ALL or AL2). As noted in previously incorporated U.S. Pat. No. 7,390,662, when light interacts with a particle, some of the incident light changes direction through the scattering process (i.e. light scatter) and part of the light is absorbed by the particles. Both of these processes remove energy from the incident beam. When viewed along the incident axis of the beam, the light loss can be referred to as forward extinction or axial light loss. Additional aspects of axial light loss measurement techniques are described in U.S. Pat. No. 7,390,662 at column 5, line 58 to column 6, line 4.

As such, the cellular analysis system 300 provides means for obtaining light propagation measurements, including light scatter and/or light transmission, for light emanating from the irradiated cells of the biological sample at any of a variety of angles or within any of a variety of angular ranges, including ALL and multiple distinct light scatter or propagation angles. For example, light detection assembly 350, including appropriate circuitry and/or processing units, provides a means for detecting and measuring UMALS, LMALS, LALS, MALS, and ALL.

Wires or other transmission or connectivity mechanisms can transmit signals from the electrode assembly (e.g. electrodes 334, 336), light scatter detector unit 350A, and/or light scatter and transmission detector unit 350B to analysis system 304 for processing. For example, measured DC impedance, RF conductivity, light transmission, and/or light scatter parameters can be provided or transmitted to analysis system 304 for data processing. In some instances, analysis system 304 may include computer processing features and/ or one or more modules or components such as those described herein with reference to the system depicted in FIG. 6, which can evaluate the measured parameters, identify and enumerate biological sample constituents, and correlate a subset of data characterizing elements of the biological sample with an immature platelet status of the individual. As shown here, cellular analysis system 300 may generate or output a report 306 containing the predicted immature platelet status and/or a prescribed treatment regimen for the individual. In some instances, excess biological sample from transducer module 310 can be directed to an external (or alternatively internal) waste system 308. In some instances, a cellular analysis system 300 may include one or more features of a transducer module or blood analysis instrument such as those described in previously incorporated U.S. Pat. Nos. 5,125,737; 6,228,652; 8,094, 299; and 8,189,187.

Figure 4:
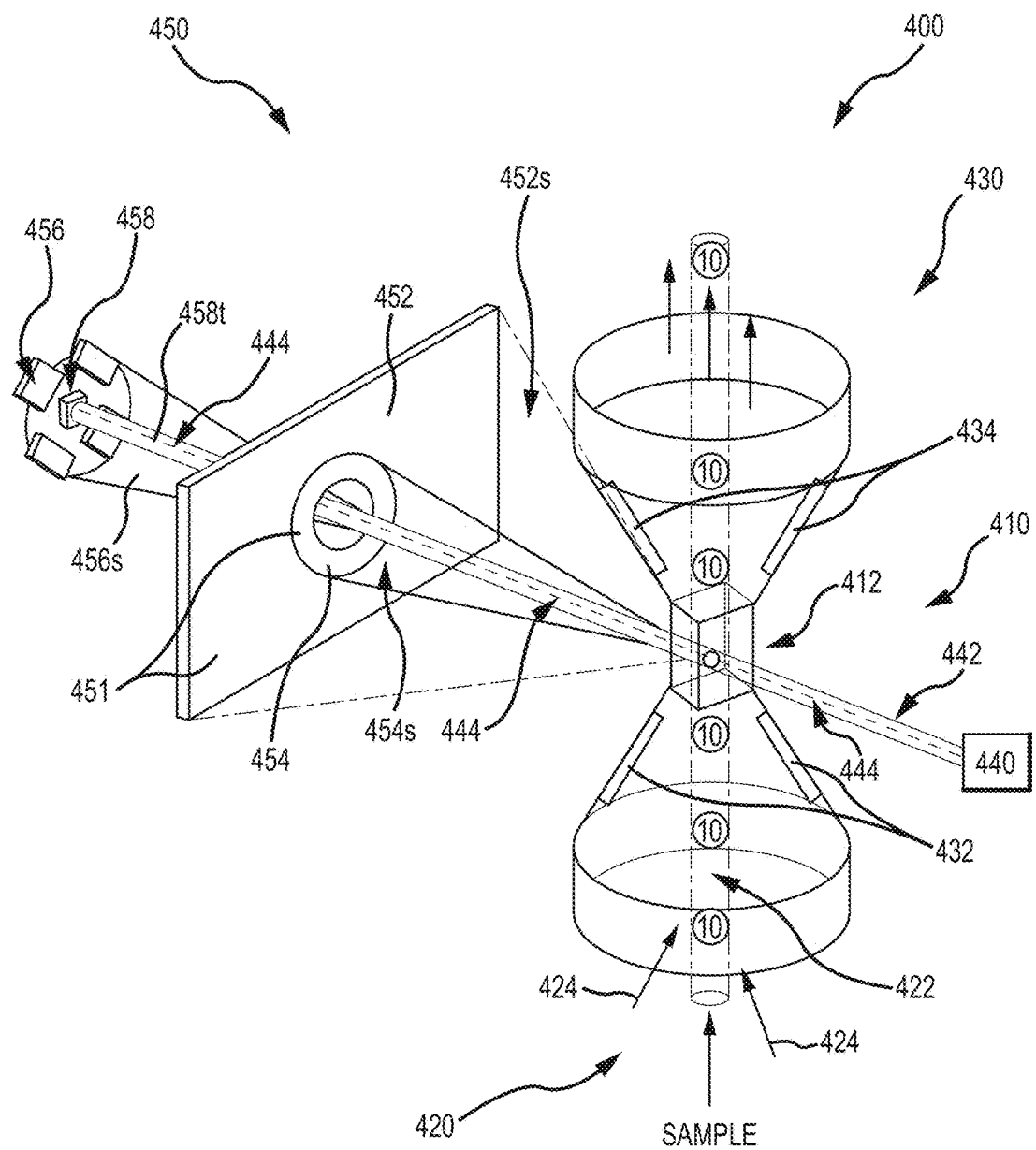
FIG. 4 illustrates aspects of an automated cellular analysis system for evaluating the immature platelet status of an individual, according to embodiments of the present invention.

FIG. 4 illustrates aspects of an automated cellular analysis system for predicting or assessing an immature platelet status of an individual, according to embodiments of the present invention. In particular, the platelet status can be predicted based on a biological sample obtained from blood of the individual. As shown here, an analysis system or transducer 400 may include an optical element 410 having a cell interrogation zone 412. The transducer also provides a flow path 420, which delivers a hydrodynamically focused stream 422 of a biological sample toward the cell interrogation zone 412. For example, as the sample stream 422 is projected toward the cell interrogation zone 412, a volume of sheath fluid 424 can also enter the optical element 410 under pressure, so as to uniformly surround the sample stream 422 and cause the sample stream 422 to flow through the center of the cell interrogation zone 412, thus achieving hydrodynamic focusing of the sample stream. In this way, individual cells of the biological sample, passing through the cell interrogation zone one cell at a time, can be precisely analyzed.

Transducer module or system 400 also includes an electrode assembly 430 that measures direct current (DC) impedance and radiofrequency (RF) conductivity of cells 10 of the biological sample passing individually through the cell interrogation zone 412. The electrode assembly 430 may include a first electrode mechanism 432 and a second electrode mechanism 434. As discussed elsewhere herein, low-frequency DC measurements can be used to analyze the volume of each individual cell passing through the cell interrogation zone. Relatedly, high-frequency RF current measurements can be used to determine the conductivity of cells passing through the cell interrogation zone. Such conductivity measurements can provide information regarding the internal cellular content of the cells. For example, high frequency RF current can be used to analyze nuclear and granular constituents, as well as the chemical composition of the cell interior, of individual cells passing through the cell interrogation zone.

The system 400 also includes a light source 440 oriented to direct a light beam 442 along a beam axis 444 to irradiate the cells 10 of the biological sample individually passing through the cell interrogation zone 412. Relatedly, the system 400 includes a light detection assembly 450 optically coupled with the cell interrogation zone, so as to measure light scattered by and transmitted through the irradiated cells 10 of the biological sample. The light detection assembly 450 can include a plurality of light sensor zones that detect and measure light propagating from the cell interrogation zone 412. In some instances, the light detection assembly detects light propagated from the cell interrogation zone at various angles or angular ranges relative to the irradiating beam axis. For example, light detection assembly 450 can detect and measure light that is scattered at various angles by the cells, as well as light that is transmitted axially by the cells along the beam axis. The light detection assembly 450 can include a first sensor zone 452 that measures a first scattered or propagated light 452$s$ within a first range of angles relative to the light beam axis 444. The light detection assembly 450 can also include a second sensor zone 454 that measures a second scattered or propagated light 454$s$ within a second range of angles relative to the light beam axis 444. As shown here, the second range of angles for scattered or propagated light 454$s$ is different from the first range of angles for scattered or propagated light 452$s$. Further, the light detection assembly 450 can include a third sensor zone 456 that measures a third scattered or propagated light 456$s$ within a third range of angles relative to the light beam axis 444. As shown here, the third range of angles for scattered or propagated light 456$s$ is different from both the first range of angles for scattered or propagated light 452$s$ and the second range of angles for scattered or propagated light 454$s$. The light detection assembly 450 also includes a fourth sensor zone 458 that measures axial light 458$t$ transmitted through the cells of the biological sample passing individually through the cell interrogation zone 412 or propagated from the cell interrogation zone along the axis beam. In some instances, each of the sensor zones 452, 454, 456, and 458 are disposed at a separate sensor associated with that specific sensor zone. In some instances, one or more of the sensor zones 452, 454, 456, and 458 are disposed on a common sensor of the light detection assembly 450. For example, the light detection assembly may include a first sensor 451 that includes first sensor zone 452 and second sensor zone 454. Hence, a single sensor may be used for detecting or measuring two or more types (e.g. low angle, medium angle, or high angle) of light scatter or propagation.

Figure 4A:
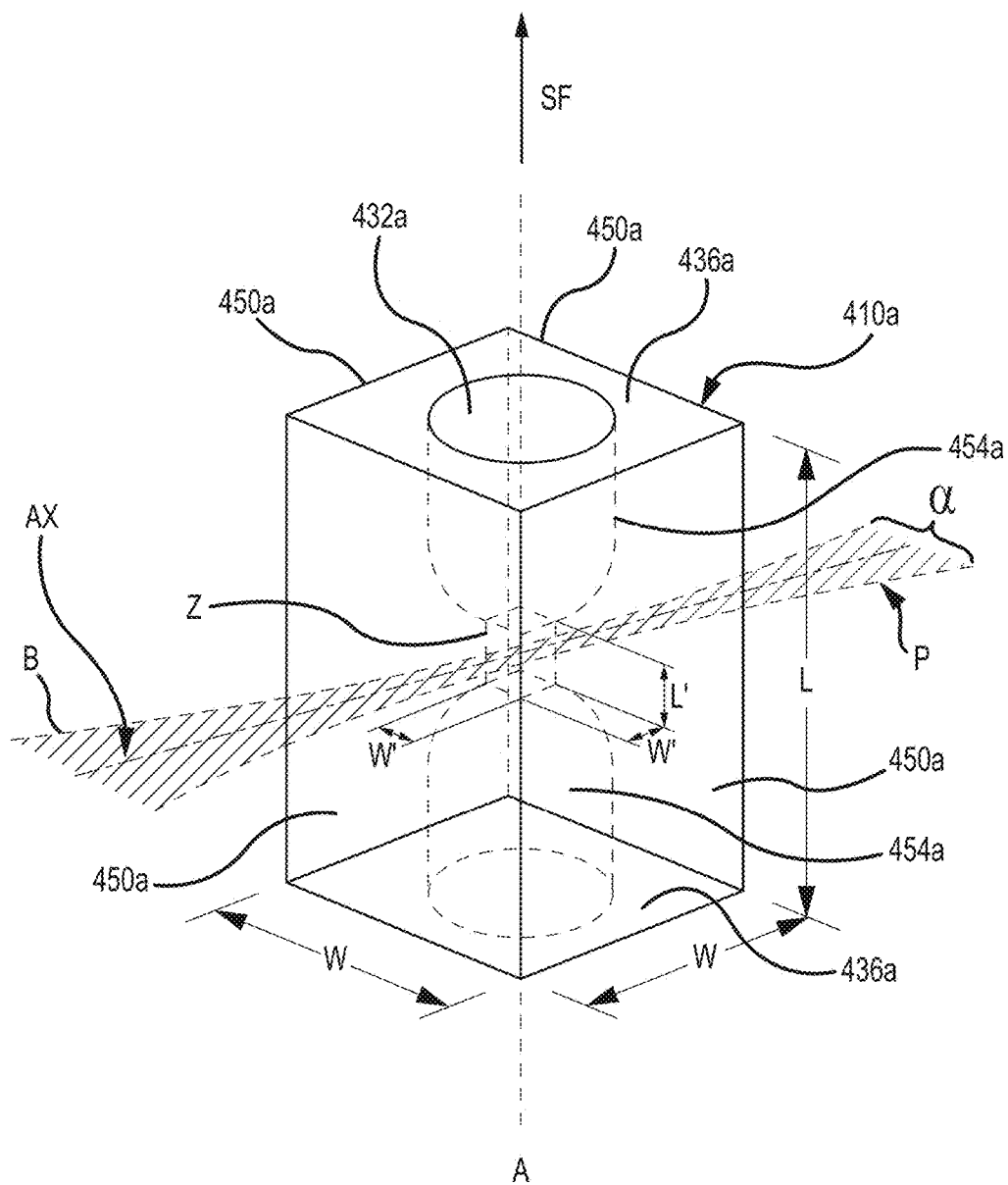
FIG. 4A shows aspects of an optical element of a cellular analysis system, according to embodiments of the present invention.

Automated cellular analysis systems may include any of a variety of optical elements or transducer features. For example, as depicted in FIG. 4A, an optical element 410$a$ of a cellular analysis system transducer may have a square prism shape, with four rectangular, optically flat sides 450$a$ and opposing end walls 436$a$. In some instances, the respective widths W of each side 450$a$ are the same, each measuring about 4.2 mm, for example. In some instances, the respective lengths L of each side 450$a$ are the same, each measuring about 6.3 mm, for example. In some instances, all or part of the optical element 410$a$ may be fabricated from fused silica, or quartz. A flow passageway 432$a$ formed through a central region of optical element 410$a$ may be concentrically configured with respect to a longitudinal axis A passing through the center of element 410$a$ and parallel to a direction of sample-flow as indicated by arrow SF. Flow passageway 432$a$ includes a cell interrogation zone Z and a pair of opposing tapered bore holes 454$a$ having openings in the vicinity of their respective bases that fluidically communicate with the cell interrogation zone. In some instances, the transverse cross-section of the cell interrogation zone Z is square in shape, the width W' of each side nominally measuring 50 microns±10 microns. In some instances, the length L' of the cell interrogation zone Z, measured along axis A, is about 1.2 to 1.4 times the width W' of the interrogation zone. For example, the length L' may be about 65 microns AO microns. As noted elsewhere herein, DC and RF measurements can be made on cells passing through the cell interrogation zone. In some instances, the maximum diameter of the tapered bore holes 454$a$, measured at end walls 436$a$, is about 1.2 mm. An optical structure 410$a$ of the type described can be made from a quartz square rod containing a 50×50 micron capillary opening, machined to define the communicating bore holes 454$a$, for example. A laser or other irradiation source can produce a beam B that is directed through or focused into the cell interrogation zone. For example, the beam may be focused into an elliptically shaped waist located within the interrogation zone Z at a location through which the cells are caused to pass. A cellular analysis system may include a light detection assembly that is configured to detect light which emanates from the optical element 410a, for example light P that is propagated from the cell interrogation zone Z which contains illuminated or irradiated cells flowing therewithin. As depicted here, light P can propagate or emanate from the cell interrogation zone Z within an angular range α, and thus can be measured or detected at selected angular positions or angular ranges relative to the beam axis AX. Relatedly, a light detection assembly can detect light scattered or axially transmitted in a forward plane within various angular ranges with respect to an axis AX of beam B. As discussed elsewhere herein, one or more light propagation measurements can be obtained for individual cells passing through the cell interrogation zone one at a time. In some cases, a cellular analysis system may include one or more features of a transducer or cell interrogation zone such as those described in U.S. Pat. Nos. 5,125,737; 6,228,652; 8,094,299; and 8,189,187, the contents of which are incorporated herein by reference.

Figure 5:
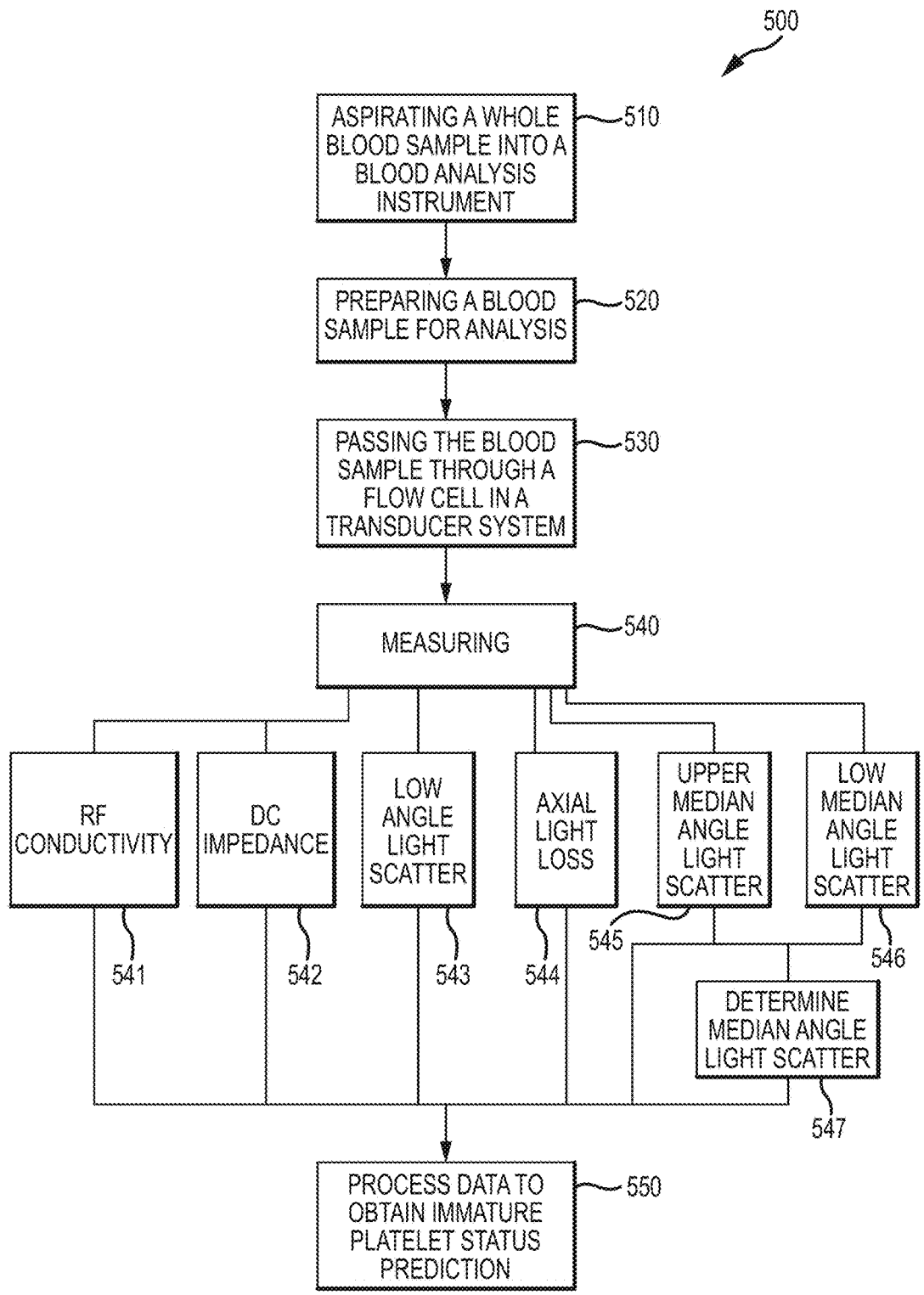
FIG. 5 depicts aspects of an exemplary method for evaluating the immature platelet status of an individual, according to embodiments of the present invention.

FIG. 5 depicts aspects of an exemplary method 500 for predicting or assessing an immature platelet status of an individual. Method 500 includes introducing a blood sample into a blood analysis system, as indicated by step 510. As shown in step 520, the method may also include preparing the blood sample by dividing the sample into aliquots and mixing the aliquot samples with appropriate reagents. In step 530, the samples can be passed through a flow cell in a transducer system such that sample constituents (e.g. blood cells) pass through a cell interrogation zone in a one by one fashion. The constituents can be irradiated by a light source, such as a laser. In step 540, any combination RF conductivity 541, DC impedance 542, first angular light propagation 543 (e.g. LALS), second angular light propagation 544 (e.g. AL2), third angular light propagation 545 (e.g. UMAL), and/or fourth angular light propagation 546 (e.g. LMALS) may be measured. As depicted by step 547, the third and fourth angular light propagation measurements can be used to determine a fifth angular light propagation measurement (e.g. MALS). Alternatively, MALS can be measured directly. As discussed elsewhere herein, certain measurements or combinations of measurements can be processed, as indicated by step 550, so as to provide an immature platelet status prediction. Optionally, methods may also include determining a treatment regime based on the predicted immature platelet status.

A cellular analysis system may be configured to correlate a subset of DC impedance, RF conductivity, angular light measurements (e.g. first scattered light, second scattered light) and the axial light measurements from the cells of the biological sample with an immature platelet status of an individual. As discussed elsewhere herein, in some instances at least a portion of the correlation can be performed using one or more software modules executable by one or more processors, one or more hardware modules, or any combination thereof. Processors or other computer or module systems may be configured to receive as an input values for the various measurements or parameters and automatically output the predicted immature platelet status of the individual. In some instances, one or more of the software modules, processors, and/or hardware modules may be included as a component of a hematology system that is equipped to obtain multiple light angle detection parameters, such as Beckman Coulter's UniCel® DxH™ 800 Cellular Analysis System. In some instances, one or more of the software modules, processors, and/or hardware modules may be included as a component of a stand-alone computer that is in operative communication or connectivity with a hematology system that is equipped to obtain multiple light angle detection parameters, such as Beckman Coulter's UniCel® DxH 800 System. In some instances, at least a portion of the correlation can be performed by one or more of the software modules, processors, and/or hardware modules that receive data from a hematology system that is equipped to obtain multiple light angle detection parameters, such as Beckman Coulter's UniCel® DxH 800 System remotely via the internet or any other over wired and/or wireless communication network. Relatedly, each of the devices or modules according to embodiments of the present invention can include one or more software modules on a computer readable medium that is processed by a processor, or hardware modules, or any combination thereof.

Figure 6:
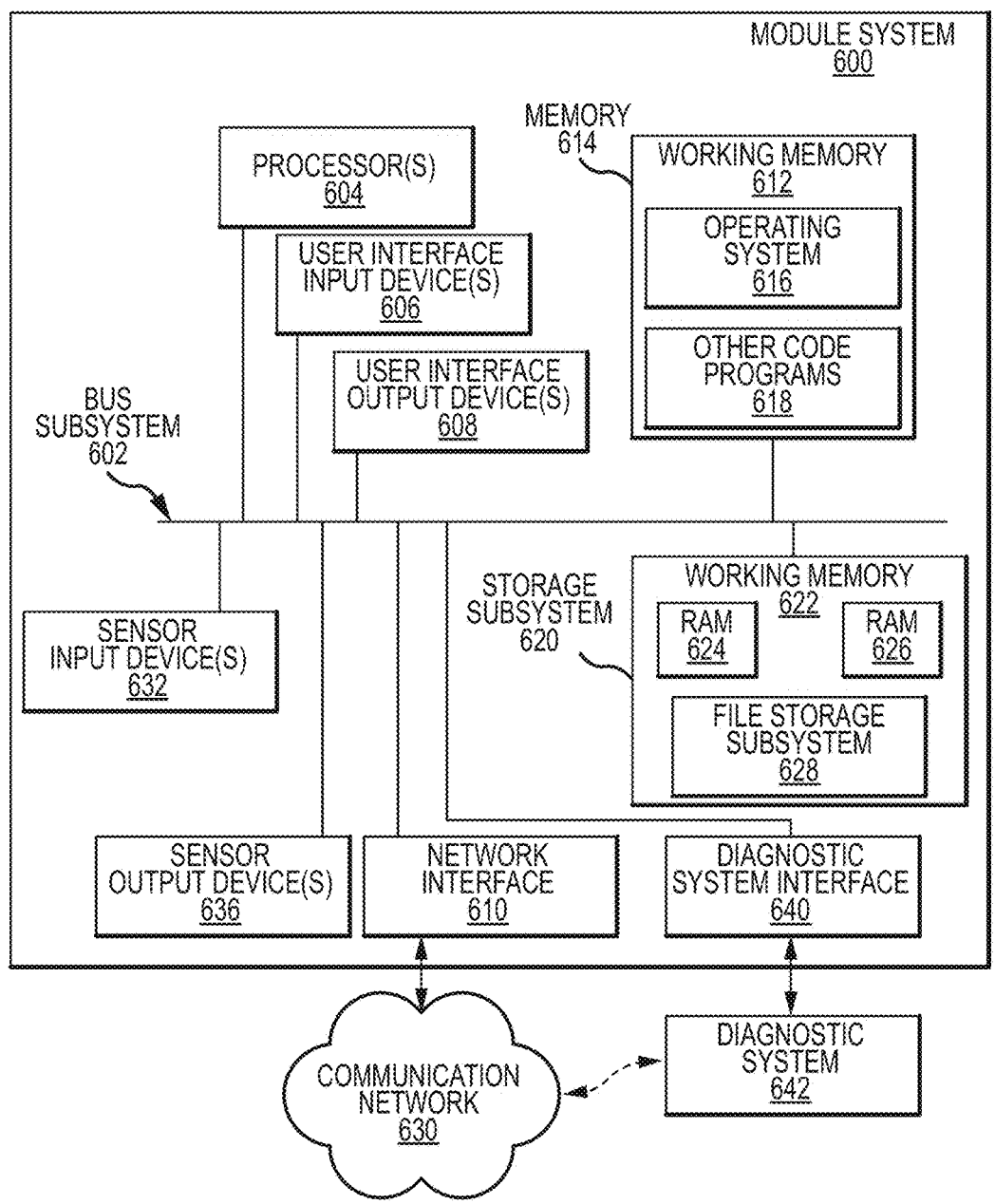
FIG. 6 provides a simplified block diagram of an exemplary module system, according to embodiments of the present invention.

FIG. 6 is a simplified block diagram of an exemplary module system that broadly illustrates how individual system elements for a module system 600 may be implemented in a separated or more integrated manner. Module system 600 may be part of or in connectivity with a cellular analysis system for predicting an immature platelet status of an individual according to embodiments of the present invention. Module system 600 is well suited for producing data or receiving input related to a platelet analysis. In some instances, module system 600 includes hardware elements that are electrically coupled via a bus subsystem 602, including one or more processors 604, one or more input devices 606 such as user interface input devices, and/or one or more output devices 608 such as user interface output devices. In some instances, system 600 includes a network interface 610, and/or a diagnostic system interface 640 that can receive signals from and/or transmit signals to a diagnostic system 642. In some instances, system 600 includes software elements, for example shown here as being currently located within a working memory 612 of a memory 614, an operating system 616, and/or other code 618, such as a program configured to implement one or more aspects of the techniques disclosed herein.

In some embodiments, module system 600 may include a storage subsystem 620 that can store the basic programming and data constructs that provide the functionality of the various techniques disclosed herein. For example, software modules implementing the functionality of method aspects, as described herein, may be stored in storage subsystem 620. These software modules may be executed by the one or more processors 604. In a distributed environment, the software modules may be stored on a plurality of computer systems and executed by processors of the plurality of computer systems. Storage subsystem 620 can include memory subsystem 622 and file storage subsystem 628. Memory subsystem 622 may include a number of memories including a main random access memory (RAM) 626 for storage of instructions and data during program execution and a read only memory (ROM) 624 in which fixed instructions are stored. File storage subsystem 628 can provide persistent (non-volatile) storage for program and data files, and may include tangible storage media which may optionally embody patient, treatment, assessment, or other data. File storage subsystem 628 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 600. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 628. In some embodiments, the software or code will provide protocol to allow the module system 600 to communicate with communication network 630. Optionally, such communications may include dial-up or internet connection communications.

It is appreciated that system 600 can be configured to carry out various aspects of methods of the present invention. For example, processor component or module 604 can be a microprocessor control module configured to receive cellular parameter signals from a sensor input device or module 632, from a user interface input device or module 606, and/or from a diagnostic system 642, optionally via a diagnostic system interface 640 and/or a network interface 610 and a communication network 630. In some instances, sensor input device(s) may include or be part of a cellular analysis system that is equipped to obtain multiple light angle detection parameters, such as Beckman Coulter's UniCel® DxH™ 800 Cellular Analysis System. In some instances, user interface input device(s) 606 and/or network interface 610 may be configured to receive cellular parameter signals generated by a cellular analysis system that is equipped to obtain multiple light angle detection parameters, such as Beckman Coulter's UniCel® DxH™ 800 Cellular Analysis System. In some instances, diagnostic system 642 may include or be part of a cellular analysis system that is equipped to obtain multiple light angle detection parameters, such as Beckman Coulter's UniCel® DxH™ 800 Cellular Analysis System.

Processor component or module 604 can also be configured to transmit cellular parameter signals, optionally processed according to any of the techniques disclosed herein, to sensor output device or module 636, to user interface output device or module 608, to network interface device or module 610, to diagnostic system interface 640, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, MacIntosh, and Unix, along with any of a variety of commonly used programming languages, may be used to implement embodiments of the present invention.

User interface input devices 606 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 606 may also download a computer executable code from a tangible storage media or from communication network 630, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 600.

User interface output devices 606 may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 600 to a user.

Bus subsystem 602 provides a mechanism for letting the various components and subsystems of module system 600 communicate with each other as intended or desired. The various subsystems and components of module system 600 need not be at the same physical location but may be distributed at various locations within a distributed network. Although bus subsystem 602 is shown schematically as a single bus, alternate embodiments of the bus subsystem may utilize multiple busses.

Network interface 610 can provide an interface to an outside network 630 or other devices. Outside communication network 630 can be configured to effect communications as needed or desired with other parties. It can thus receive an electronic packet from module system 600 and transmit any information as needed or desired back to module system 600. As depicted here, communication network 630 and/or diagnostic system interface 642 may transmit information to or receive information from a diagnostic system 642 that is equipped to obtain multiple light angle detection parameters, such as such as Beckman Coulter's UniCel® DxH™ 800 Cellular Analysis System.

In addition to providing such infrastructure communications links internal to the system, the communications network system 630 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 600 itself can be of varying types including a computer terminal, a personal computer, a portable computer, a workstation, a network computer, or any other data processing system. Due to the ever-changing nature of computers and networks, the description of module system 600 depicted in FIG. 6 is intended only as a specific example for purposes of illustrating one or more embodiments of the present invention. Many other configurations of module system 600 are possible having more or less components than the module system depicted in FIG. 6. Any of the modules or components of module system 600, or any combinations of such modules or components, can be coupled with, or integrated into, or otherwise configured to be in connectivity with, any of the cellular analysis system embodiments disclosed herein. Relatedly, any of the hardware and software components discussed above can be integrated with or configured to interface with other medical assessment or treatment systems used at other locations.

In some embodiments, the module system 600 can be configured to receive one or more cellular analysis parameters of a patient at an input module. Cellular analysis parameter data can be transmitted to an assessment module where an immature platelet status is predicted or determined. The predicted immature platelet status can be output to a system user via an output module. In some cases, the module system 600 can determine an initial treatment or induction protocol for the patient, or an adjusted treatment protocol, based on one or more cellular analysis parameters and/or the predicted immature platelet status, for example by using a treatment module. The treatment can be output to a system user via an output module. Optionally, certain aspects of the treatment can be determined by an output device, and transmitted to a treatment system or a sub-device of a treatment system. Any of a variety of data related to the patient can be input into the module system, including age, weight, sex, treatment history, medical history, and the like. Parameters of treatment regimens or diagnostic evaluations can be determined based on such data.

Relatedly, in some instances a system includes a processor configured to receive VCS data as input. A processor may also be configured to receive CBC data as input. Optionally, a processor, storage medium, or both, may be incorporated within a hematology or cellular analysis machine. In some instances, the hematology machine may generate VCS data, CBC data, or other information for input into the processor. In some instances, a processor, a storage medium, or both, can be incorporated within a computer, and the computer can be in communication with a hematology machine. In some instances, a processor, a storage medium, or both, can be incorporated within a computer, and the computer can be in remote communication with a hematology machine via a network.

Volume Conductivity Scatter (VCS) Data

In addition to CBC data, which may be obtained from a CBC module, VCS data may be obtained from a VCS module. Exemplary VCS parameters include the following:
1. Cell Conductivity (C) [high frequency current]
2. Cell Volume (V) [low frequency current]
3. Axial light loss or absorbed light (AL2 or ALL)
4. Low-angle light scatter (LALS)
5. Upper median-angle light scatter (UMALS)
6. Lower median-angle light scatter (LMALS)
7. Median-angle light scatter (MALS) [UMALS+LMALS]

In this way, various parameters (e.g. volume, conductivity, and angles of light scatter or propagation) can be calculated separately for blood cells such as white blood cells, red blood cells, and platelets. This data can be obtained based on a biological sample of an individual. What is more, CBC and VCS data can be viewed on the screen of an instrument, such as that depicted in FIG. 7, as well as automatically exported as an Excel file. Hence, blood cells (e.g. RBC's, platelets, and WBC's) can be analyzed and individually plotted in tri-dimensional histograms, with the position of each cell on the histogram being defined by certain parameters as described herein.

Figure 7:
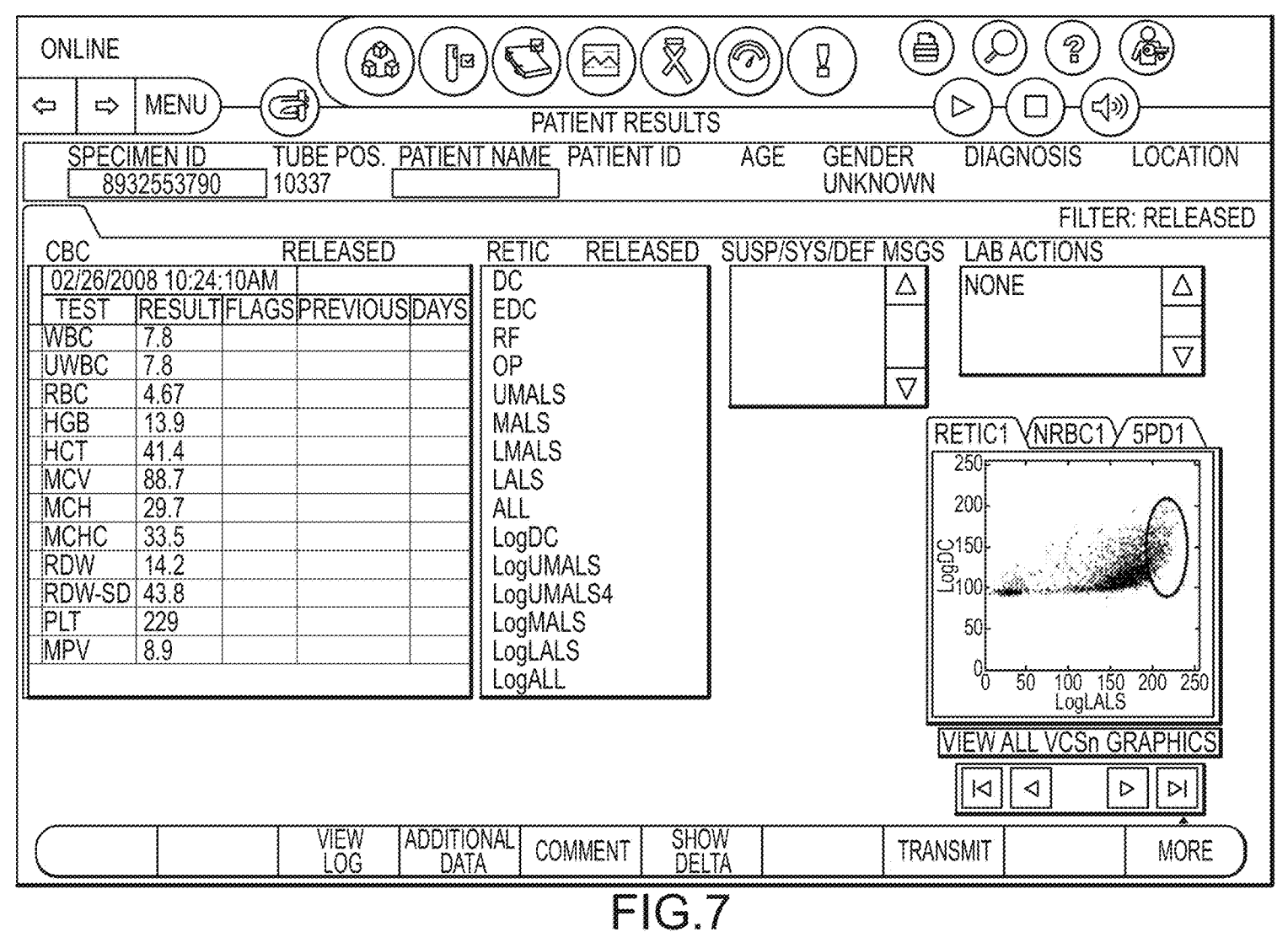

Subpopulations of cells can be separated into different groups at different locations on the histograms. For example, immature platelets and mature platelets can be clustered in different regions of a histogram, thus forming cell populations. FIG. 7 depicts an exemplary screen shot of a count analysis. As illustrated here, the immature platelets are encircled on the histogram. Generally, such histograms can be obtained from a reticulocyte channel (or a WBC differential channel or an NRBC channel) as discussed elsewhere herein.

Figure 7A:
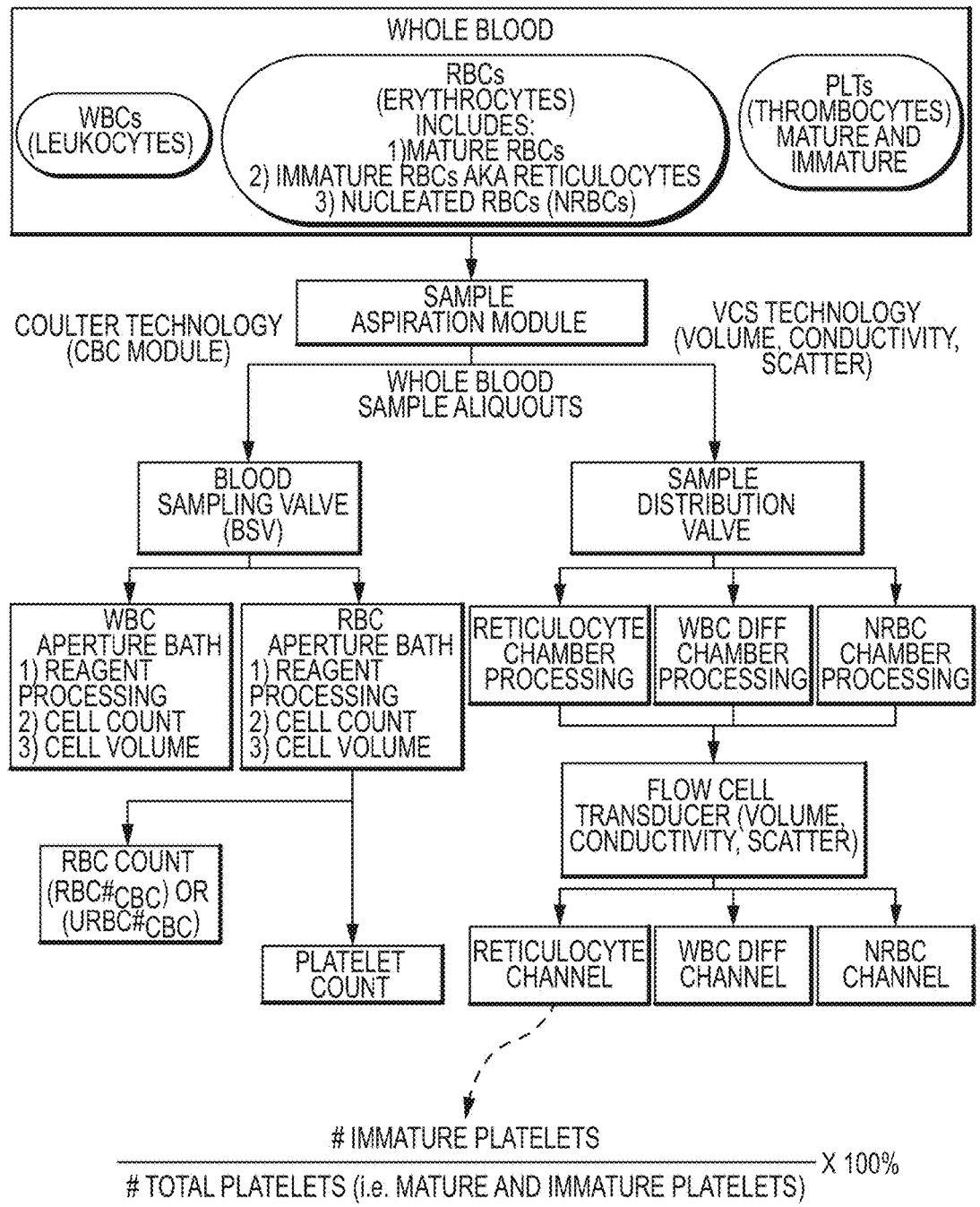
FIG. 7A schematically shows a technique for obtaining blood cell parameters, according to embodiments of the present invention.
Figure 7B:
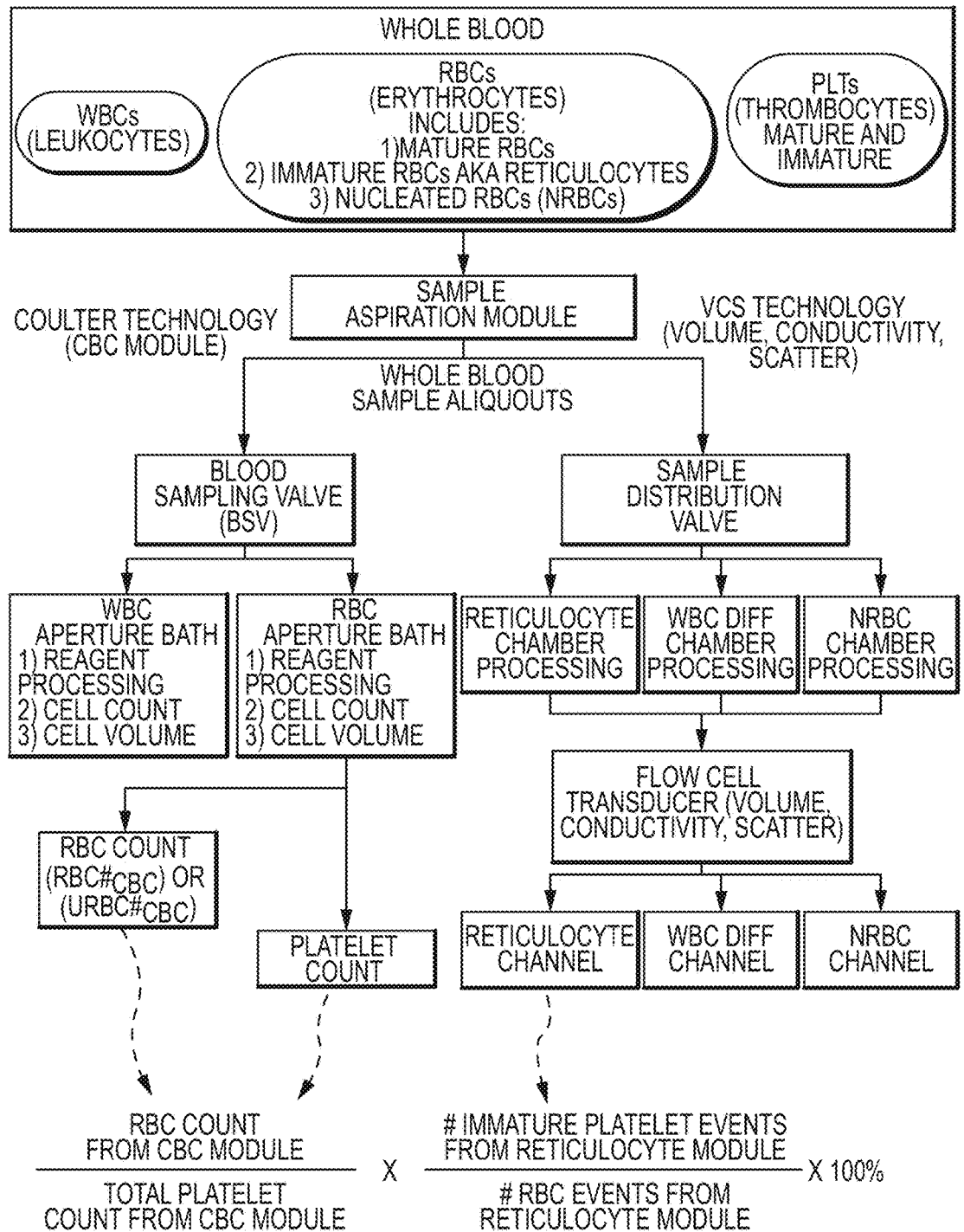
FIG. 7B schematically shows a technique for obtaining blood cell parameters, according to embodiments of the present invention.
Figure 7C:
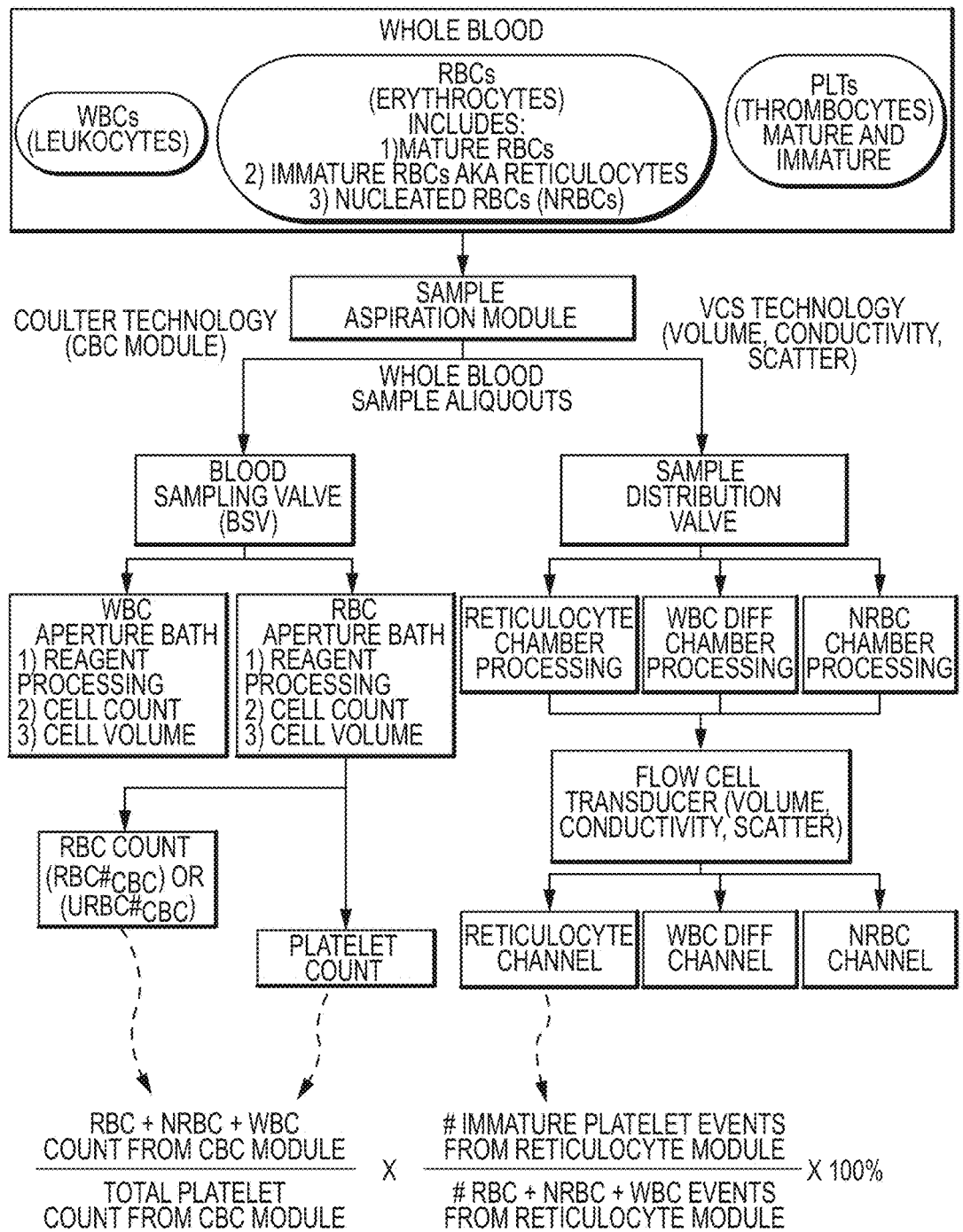
FIG. 7C schematically shows a technique for obtaining blood cell parameters, according to embodiments of the present invention.

Such VCS values can correspond to the position of the population in the histogram, and to the morphology of the blood cells under the microscope. As depicted in FIGS. 7A to 7C, certain channel modules can provide measurements for various blood components, such as blood cells or cellular debris which may be present.

VCS parameters can be used to analyze cellular events in a quantitative, objective, and automated manner, free from the subjectivity of human interpretation, which is also very time consuming, expensive, and has limited reproducibility. VCS parameters can be used in the diagnosis of various medical conditions that alter the immature platelet counts or percentages. It is understood that when referring to VCS parameters or volume conductivity scatter data profiles, such characterizations may include a subset of the individual VCS data features. For example, VCS parameter data may include a combination of volume and conductivity measures, a combination of volume and scatter measures, or a combination of conductivity and scatter measures. Similarly, VCS parameter data may include a volume measure only, a conductivity measure only, or a scatter measure only. In some instances, VCS parameter data may be considered to include a set or subset of light propagation and current data. For example, the light propagation measures may include a first propagated light at a first angle, a second propagated light at a second angle different from the first angle, an axial propagated light, or any combination thereof. Relatedly, the current measures may include a low frequency current (e.g DC impedance corresponding to volume), a high frequency current (e.g. RF conductivity corresponding to internal cellular density), or a combination thereof. In this sense, VCS parameter data or volume conductivity scatter data profiles may be referred to as current light propagation parameters or data profiles.

As further discussed herein, it has been discovered that certain VCS parameter values are highly useful for assessing an immature platelet status in an individual. Accordingly, these parameters can be implemented in systems and methods for the diagnosis of platelet-related conditions.

FIG. 7A illustrates aspects of a biological sample analysis system, according to embodiments of the present invention. As depicted here, immature platelet analysis techniques may include determining both an immature platelet count and a mature platelet count using a VCS reticulocyte channel. Further, techniques may include calculating an immature platelet percent (IP %) as the percentage of immature platelets with respect to the total platelets, by directly calculating the number of the immature platelet events divided by the number of both mature and immature platelet events, multiplied by 100%.

FIG. 7B illustrates aspects of a biological sample analysis system, according to embodiments of the present invention. As depicted here, immature platelet analysis techniques may include determining an RBC count and a total platelet count using a CBC module, and determining an immature platelet count and an RBC count using a reticulocyte channel of a VCS module. Further, techniques may include calculating an immature platelet percent (IP %) as the ratio of RBC events to total platelet events (obtained via the CBC module) multiplied by the ratio of immature platelet events to RBC events (obtained via the VCS module), multiplied by 100%. In some instances, the event count from the CBC module RBC aperture bath includes RBC events. The event count from the CBC module RBC aperture bath may also include immature platelet events and mature platelet events.

FIG. 7C illustrates aspects of a biological sample analysis system, according to embodiments of the present invention. As depicted here, immature platelet analysis techniques may include determining an RBC+NRBC+WBC count and a total platelet count using a CBC module, and determining an immature platelet count and an RBC+NRBC+WBC count using a reticulocyte channel of a VCS module. Further, techniques may include calculating an immature platelet percent (IP %) as the ratio of RBC+NRBC+WBC events to total platelet events (obtained via the CBC module) multiplied by the ratio of immature platelet events to RBC+NRBC+WBC events (obtained via the VCS module), multiplied by 100%. In some instances, an event count from the CBC module RBC aperture bath includes RBC events, NRBC events, and WBC events. In some instances, an event count from the CBC module RBC aperture bath includes immature platelet events and mature platelet events.

Figure 8:
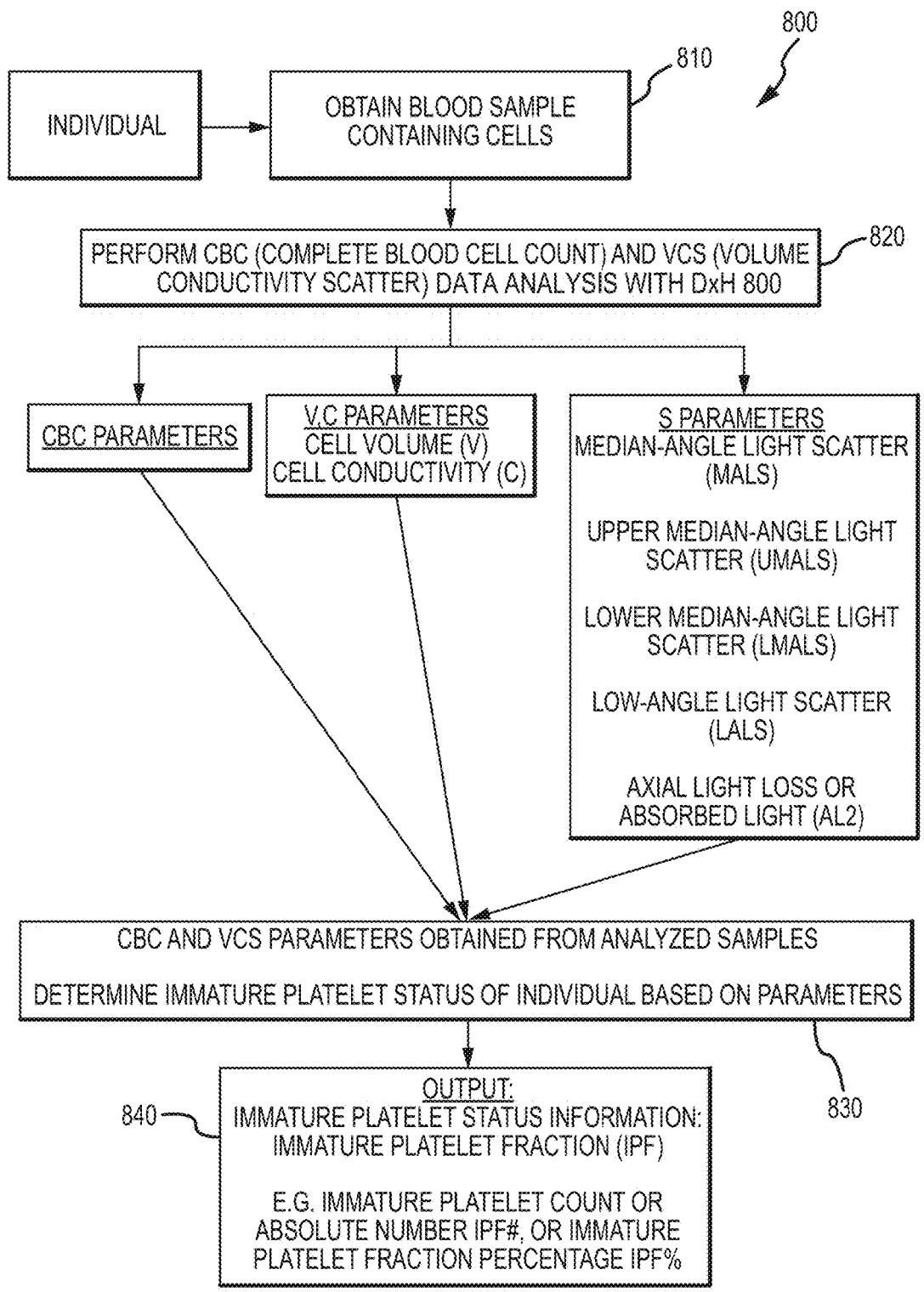
FIG. 8 illustrates aspects of a method for determining immature platelet status information based on a biological sample obtained from an individual, according to embodiments of the present invention.

FIG. 8 schematically illustrates a method 800 for obtaining an immature platelet parameter (e.g. count or percentage) according to embodiments of the present invention. As depicted here, the method includes obtaining blood samples from individuals (e.g. during routine examinations), as indicated by step 810. Complete Blood Count (CBC) data, Volume Conductivity Scatter (VCS) data, or combinations thereof, can be obtained from these biological samples, using a cellular analysis system that is equipped to obtain cellular event parameters, such as Beckman Coulter's UniCel® DxH 800 System, as indicated by step 820. CBC parameters, VCS parameters, or combinations thereof from analyzed samples can be used to determine the immature platelet parameters, as indicated by step 830. Methods may also include outputting immature platelet status information, as indicated in step 840.

Analysis Systems

Embodiments of the present invention encompass cellular analysis systems and other automated biological investigation devices which are programmed to carry out immature platelet status prediction or identification methods according to techniques as disclosed herein. For example, a system that is equipped to obtain and/or process multiple light angle detection parameters, such as Beckman Coulter's UniCel® DxH 800 System, or processors or other computer or module systems associated therewith or incorporated therein, can be configured to receive as input values for the various measurements or parameters discussed herein, and automatically output a predicted immature platelet status. The predicted status may provide an indication that the individual has a normal immature platelet level, an elevated immature platelet level, or a depressed immature platelet level, for example. In some instances, a system that is equipped to obtain and/or process multiple light angle detection parameters, such as a Beckman Coulter UniCel® DxH 800 System, may include a processor or storage medium that is configured to automatically implement an immature platelet fraction analysis, whereby data obtained from a biological sample analyzed by a system that is equipped to obtain multiple light angle detection parameters, such as the DxH 800 System, is also processed by a system that is equipped to obtain and/or process multiple light angle detection parameters, such as the DxH 800 System, and an immature platelet prediction or indication is provided or output by the system that is equipped to obtain and/or process multiple light angle detection parameters, such as the DxH 800 System, based on the analyzed data.

Figure 9:
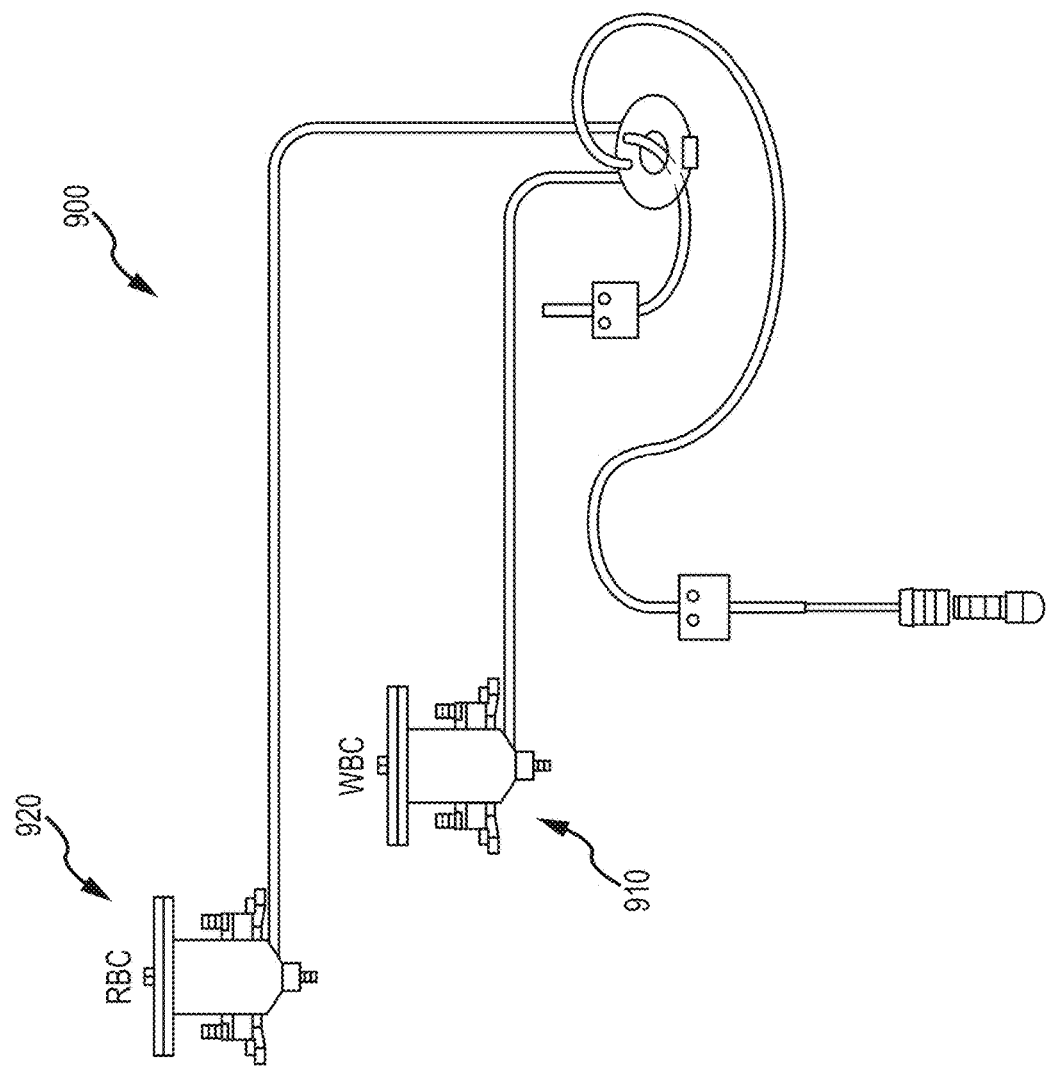
FIGS. 9 and 10 show aspects of blood cell analysis devices according to embodiments of the present invention.

FIG. 9 depicts aspects of an exemplary CBC module 900, according to embodiments of the present invention. Such CBC modules, which may be part of a system such as Beckman Coulter's UniCel® DxH 800 System, can operate to control or carry out various mechanical functions as well as electronic and photometric measurement functions for WBC, RBC and PLT cell counting and hemoglobin measurements. Exemplary CBC module can be used to prepare the samples for CBC analysis, and to generate CBC parameter measurements via aperture bath assemblies (e.g. WBC bath 910 and RBC bath 920).

Cellular elements of the blood (e.g. erythrocytes, leukocytes, and platelets) can be counted using electrical impedance methods. For example, an aspirated whole blood sample can be divided into two aliquots and mixed with an isotonic diluent. The first dilution can be delivered to the RBC aperture bath 920, and the second can be delivered to the WBC aperture bath 910. In the RBC chamber, both RBCs and platelets can be counted and discriminated by electrical impedance as the cells pass through sensing apertures. For example, particles between 2 and 20 fL can be counted as platelets, and those greater than 36 fL can be counted as RBCs. For the WBC chamber processing, an RBC-lysing reagent can be added to the WBC dilution aliquot to lyse RBCs and release hemoglobin, and then WBCs can be counted by impedance in sensing apertures of the WBC bath. In some in stances, the baths may include multiple apertures. Hence, for example, a platelet event count used in an immature platelet enumeration technique may be obtained using an RBC triple aperture bath.

An exemplary CBC sample preparation technique may include two processes, sample acquisition and sample delivery. Sample acquisition may occur when 165 uL of patient sample is aspirated and directed to a Blood Sampling Valve (BSV), for example as depicted in FIGS. 7A to 7C. The BSV can operate to direct specific volumes of the patient sample with the DxH reagents for delivery to the two triple-aperture baths. The patient sample and the DxH reagents can be delivered to the bottom of aperture baths at an angle that, with a round design, allow the sample and reagents to thoroughly mix without mixing bubbles. The sample can then be prepared for measurement and analysis. According to some embodiments, in the WBC bath, 6.0 mL (±1.0%) of DxH diluent and 28 uL of sample can be combined with 1.08 mL (±1.0%) of DxH cell lyse for a final dilution of 1:251. According to some embodiments, in the RBC bath, 10 mL (±1.0%) of DxH diluent and 1.6 uL of sample can be combined for a final dilution of 1:6250. After the patient sample and DxH reagents are mixed, vacuum and aperture current can be applied to the apertures for the measurements of cell count and cell volume. The RBC and PLT counts can also include the application of sweep flow to prevent recirculation of cells near the aperture. In certain embodiments, data acquisition for the RBC and PLT can be up to a maximum of 20 seconds and for the WBC a maximum of 10 seconds. In certain embodiments, all analog pulses generated by the aperture assemblies can be amplified by a preamp card and then sent to a CBC signal conditioner analyzer card for analog-to-digital conversion and parameter extraction. According to some embodiments, a system such as Beckman Coulter's UniCel® DxH 800 System can be used to measure multiple parameters for each cellular event, and a digital parameter extraction process can be used to provide digital measurements such as time, volume (pulse attributes including amplitude and pulse width), count and count rate, and wait time. Such measurements can be used, optionally by a system such as Beckman Coulter's UniCel® DxH 800 System, for pulse editing, coincidence correction, count voting, generation of histograms for WBC, RBC and PLT, histogram voting, pattern analysis, and interference correction, and the like.

Figure 10:
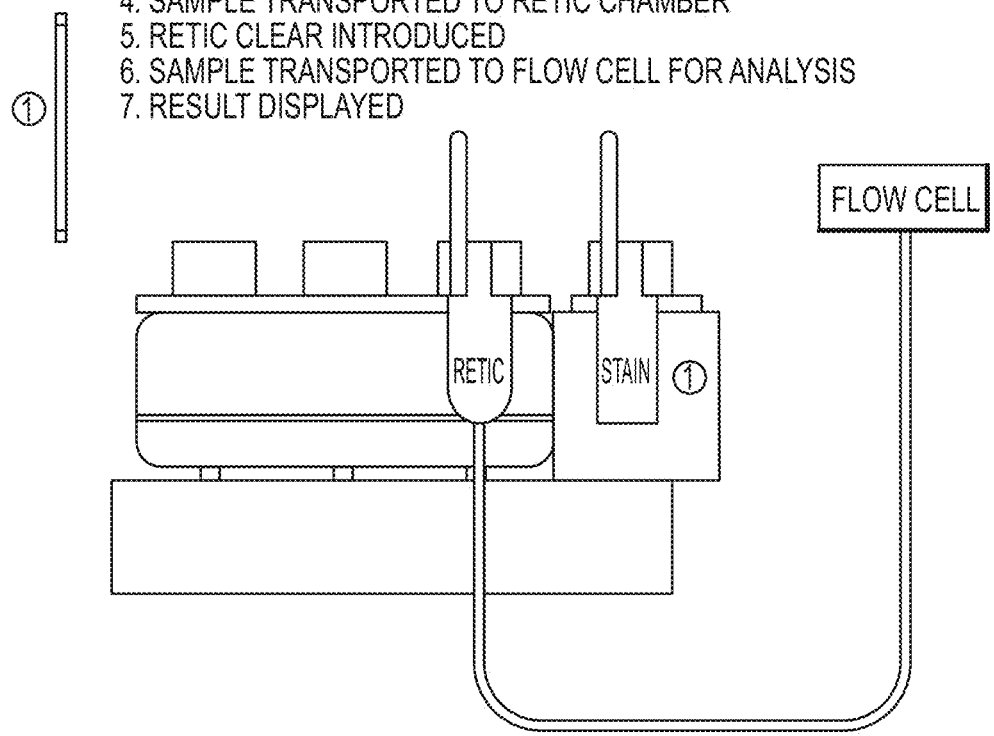

FIG. 10 depicts aspects of an exemplary reticulocyte processing chamber, according to embodiments of the present invention. According to some embodiments, a reticulocyte module of a systems such as Beckman Coulter's UniCel® DxH 800 can be used to apply a stain such as new methylene blue stain to a blood sample before the sample is processed through a signal-acquisition aperture (e.g. of a VCS module flow cell transducer). The new methylene blue stain is a non-fluorochrome dye that precipitates RNA of the immature platelets (IP's). The precipitated RNA can effectively increases measured light scatter signals collected at a variety of different angles. Embodiments of the present invention encompass the use of any of a variety of techniques for staining immature platelets, and materials other than or in addition to new methylene blue stain may be used. As shown here, a reticulocyte chamber and channel processing technique may include delivering an amount of blood (e.g. 27 µl) to a stain chamber, contacting the amount of blood with a stain (e.g by mixing the blood and stain), incubating the mixture, transporting the incubated mixture to a reticulocyte chamber, introducing a retic clear reagent, transporting an amount of the sample (e.g. 4 µl) to a flow cell for analysis, and displaying the results.

Gating Techniques

Hematology evaluations may involve simultaneous multiparametric analysis of thousands of particles per second by suspending cells in a stream of fluid and passing them by an electronic detection apparatus. The data generated can be plotted into histograms and divided into regions. Regions are shapes that are drawn or positioned around a population of interest on a one or two parameter histogram. Exemplary region shapes include two dimensional polygons, circles, ellipses, irregular shapes, or the like. Individual events exemplified in the data correspond to unique combinations of parameters, and are accumulated in cases where multiple instances of such combinations are present. When a region is used to limit or isolate cells or events that are drawn or positioned on a histogram, such that those isolated cells or events can be manifested in a subsequent histogram, this process is referred to as gating. The data accumulated into histograms can be separated or clustered based on VCS parameters, in a series of sequential steps known as "gating" involving one or more regions. In some cases, gates are combined with each other using Boolean logic (AND, OR, NOT). A common technique involves using gates sequentially. In some cases, gates are performed in parallel.

Various manual, automated, and other gating, boundary decision, region placement, or histogram segmentation techniques may be used for segmenting or gating histogram data, and exemplary techniques are discussed in US Patent Publication No. 2010/0111400 ("Non-Linear Histogram Segmentation for Particle Analysis"), the content of which is incorporated herein by reference.

Table 1 provides exemplary definitions which in certain instances may be used for various parameters or terms used herein.

TABLE 1

| | |
|---|---|
| DC | DC impedance measurement |
| EDC | 2xDC |
| RF | radio-frequency impedance measurement |
| OP | the ratio of RF to DC |
| UMALS | Upper Median Angle Light Scatter |
| MALS | Median Angle Light Scatter |
| LMALS | Lower Median Angle Light Scatter |
| LALS | Low Angle Light Scatter |
| ALL | Axial Light Loss |
| LogDC | logarithmic transformation of DC |
| LogUMALS | logarithmic transformation of UMALS |
| LogUMALS4 | logarithmic transformation of UMALS over 4 decades |
| LogMALS | logarithmic transformation of MALS |
| LogLALS | logarithmic transformation of LALS |
| LogALL | logarithmic transformation of ALL |

According to some embodiments, various gating steps can be performed to obtain an immature platelet count or percent. An exemplary protocol may include identifying debris events, identifying WBC/NRBC events, identifying platelet events, identifying RBC events, identifying immature platelet events in the platelet population, and calculating IP count or percentage. One or more of these steps can be performed based on reticulocyte module and channel processing techniques using a system such as Beckman Coulter's UniCel® DxH 800 System.

Debris Event Identification

Figure 11:
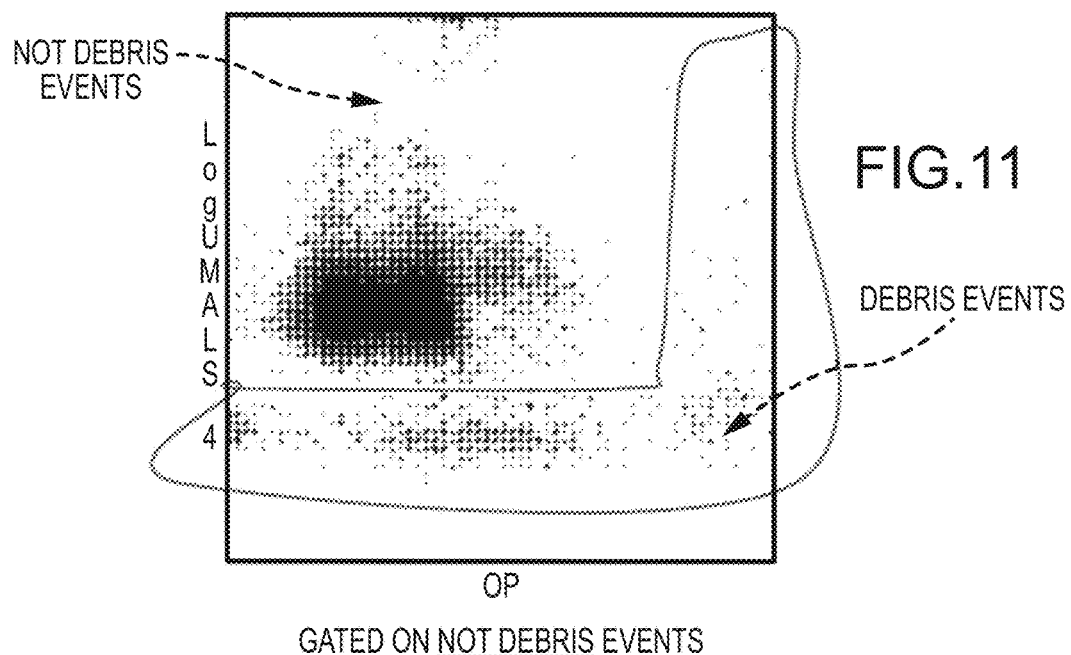
FIG. 11 depicts aspects of a gating technique according to embodiments of the present invention.

According to some embodiments of the present invention, the histograms shown in FIGS. 11 to 18 can be based on data obtained using a reticulocyte module and channel of a cellular analysis system, such as Beckman Coulter's UniCel® DxH 800 System. As shown in FIG. 11, debris events can be detected during data acquisition. Such debris events can be identified in a LogUMALS4 vs OP view. As shown here, the debris events are located at the bottom and on the right. The identified debris events can be excluded from subsequent gating steps.

As shown in the 2D histogram here (which in some embodiments originates from gated events or in certain embodiments originates from ungated events), a region named Debris and its corresponding boundary line divides the histogram into two separate sets of events. The Debris region can be defined by the boundary line, in combination with the outer limits of the histogram boundaries (maximum OP value on the right side, minimum LogUMALS4 value on the lower side). The Debris region separates the histogram into two independent sets of data. The original data shown include all events, and the region separates the events into two separate sets, such that a first set is inside of the region (Debris) and a second set is outside of the region (NOT Debris). Hence, the region is a shape that separates the data into two subsets.

The number of gated events falling within the region boundary line (i.e. lines defining the region) can be counted or assessed. As a nonlimiting example, in some embodiments this involves determining the number of events falling within the boundary line which defines the Debris region. Further, the total number of events being analyzed can be obtained. In some embodiments this number refers to a predefined subset of all collected events. In some instances, FIG. 11 may represent a gated or an ungated histogram. The term ungated as used herein means, as a nonlimiting example, that the histogram is built using all of the data available which was obtained by the instrument.

Figure 12:
FIG. 12 depicts aspects of a gating technique according to embodiments of the present invention.

In some embodiments the second region (NOT Debris) can be used to limit or isolate cells or events that are drawn or positioned on the histogram of FIG. 11, such that those isolated cells or events are manifested in the subsequent histogram of FIG. 12. In this way, the use of the region (NOT Debris) operates as a gating step, by limiting the number of events or cells from the first histogram (of FIG. 11) that are subsequently manifested in the second histogram (of FIG. 12). As a nonlimiting example, the region acts as a gate to filter out or isolate those events within the region boundaries, so that the events are extracted and placed in the next histogram. The term gated as used here means, as a nonlimiting example, that the data present in the histogram is derived using a gating step, as applied to a previous histogram.

Hence, as depicted here, FIG. 11 may represent ungated or gated data, and FIG. 12 represents gated data (i.e. gated on NOT Debris events). In many cases, the parameters of a subsequent histogram are different from those used for the previous histogram. In some cases, a population is isolated using a single gating step. In some cases, a population is isolated using multiple gating steps. As discussed elsewhere here, Boolean logic is in some situations applied to histogram data.

WBC/NRBC Event Identification

WBC and NRBC cells have a nucleus and can be identified in an ALL vs (Log MALS+Log LALS) histogram as shown in FIG. 12. The WBC/NRBC events are located in the upper right corner, which are shown as enclosed. The identified WBC/NRBC events can be excluded from subsequent gating steps.

As shown in the 2D histogram here, a region named WBC/NRBC and its corresponding boundary line divides the histogram into two separate sets of events. The WBC/NRBC region can be defined at least partially by the boundary line. The WBC/NRBC region separates the histogram into two independent sets of data, such that a first set is inside of the region (WBC/NRBC) and a second set is outside of the region (NOT WBC/NRBC). Hence, the region is a shape that separates the data into two subsets.

Figure 13:
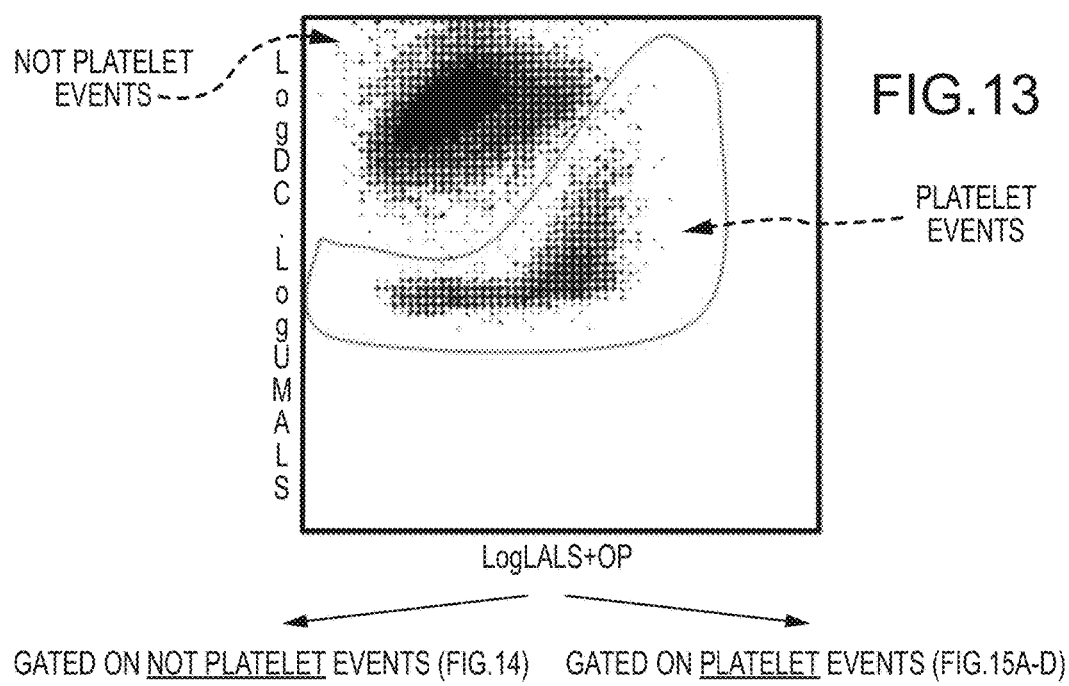
FIG. 13 depicts aspects of a gating technique according to embodiments of the present invention.

In some embodiments the second region (NOT WBC/NRBC) can be used to limit or isolate cells or events that are drawn or positioned on the histogram of FIG. 12, such that those isolated cells or events are manifested in the subsequent histogram of FIG. 13. In this way, the use of the region (NOT WBC/NRBC) operates as a gating step, by limiting the number of events or cells from the first histogram (of FIG. 12) that are subsequently manifested in the second histogram (of FIG. 13). As a nonlimiting example, the region acts as a gate to filter out or isolate those events within the region boundaries, so that the events are extracted and placed in the next histogram. The term gated as used here means, as a nonlimiting example, that the data present in the histogram is derived using a gating step, as applied to a previous histogram.

Hence, as depicted here, FIG. 13 represents gated data (i.e. gated on NOT WBC/NRBC events). In many cases, the parameters of a subsequent histogram are different from those used for the previous histogram. In some cases, a population is isolated using a single gating step. In some cases, a population is isolated using multiple gating steps. As discussed elsewhere here, Boolean logic is in some situations applied to histogram data.

Platelet Event Identification

According to some embodiments, platelet events can exhibit lower DC, higher light scatters, and higher OP. One view which can be used to separate platelet events from other events is (Log DC−LogUMALS) vs (Log LALS+OP) as shown in FIG. 13. The platelet events are located in the lower right corner, which are enclosed. As shown here, the identified platelet events can be excluded (e.g. when gating on the NOT platelet events to obtain FIG. 14) or selected (e.g. when gating on the platelet events to obtain FIGS. 15A-D).

As shown in the 2D histogram of FIG. 13, a region named Platelet and its corresponding boundary line divides the histogram into two separate sets of events. The Platelet region can be defined at least partially by the boundary line. The Platelet region separates the histogram into two independent sets of data, such that a first set is inside of the region (Platelet) and a second set is outside of the region (NOT Platelet). Hence, the region is a shape that separates the data into two subsets.

Figure 14:
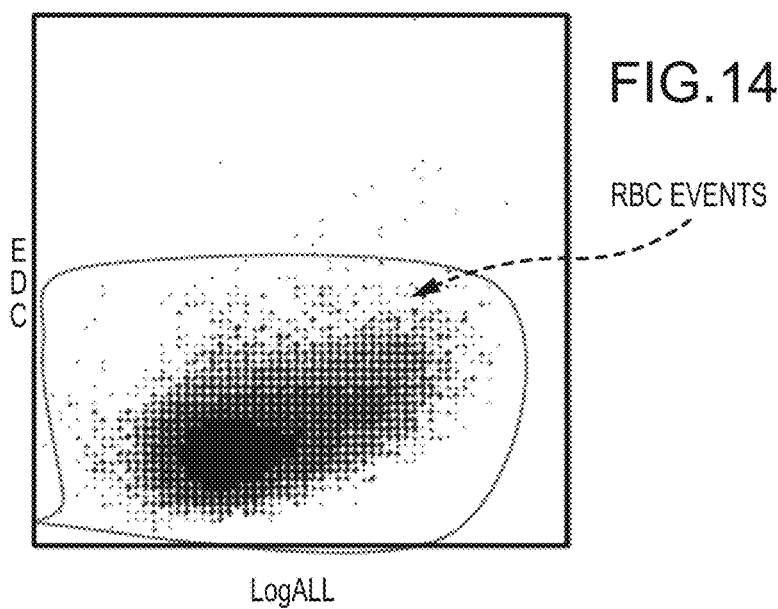
FIG. 14 depicts aspects of a gating technique according to embodiments of the present invention.
Figure 16A:
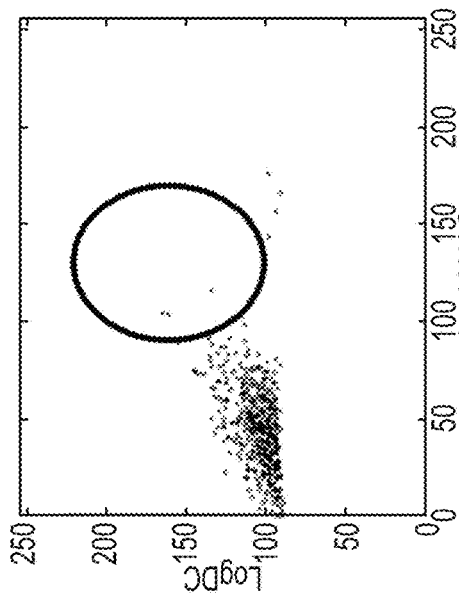
FIGS. 16A to 16D depict aspects of a gating technique according to embodiments of the present invention.
Figure 16B:
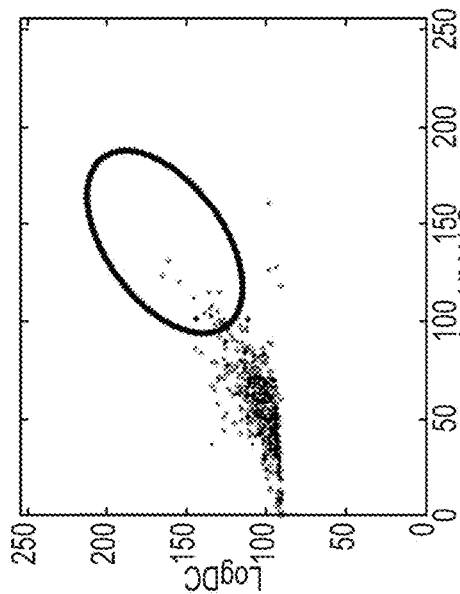
Figure 16C:
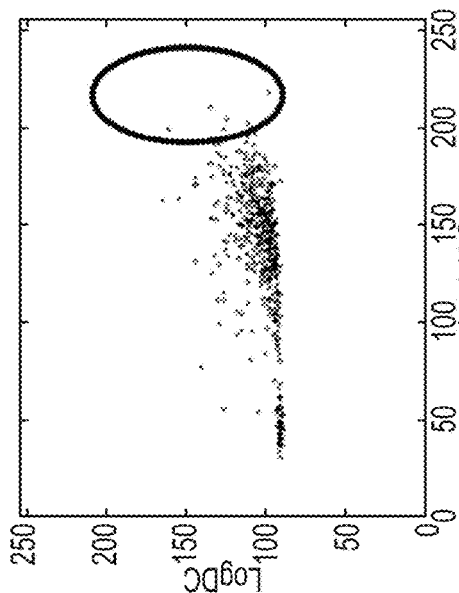
Figure 16D:
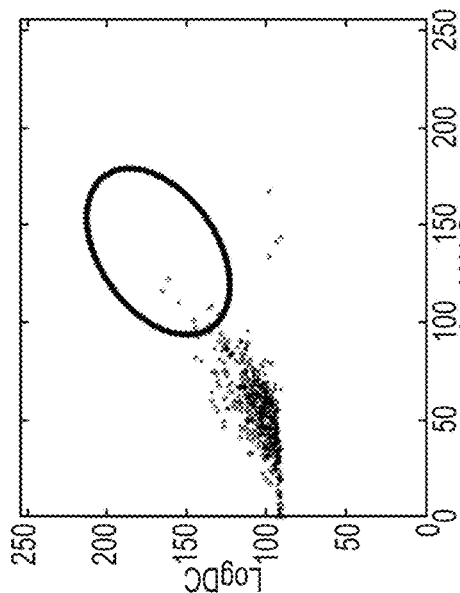
Figure 17:
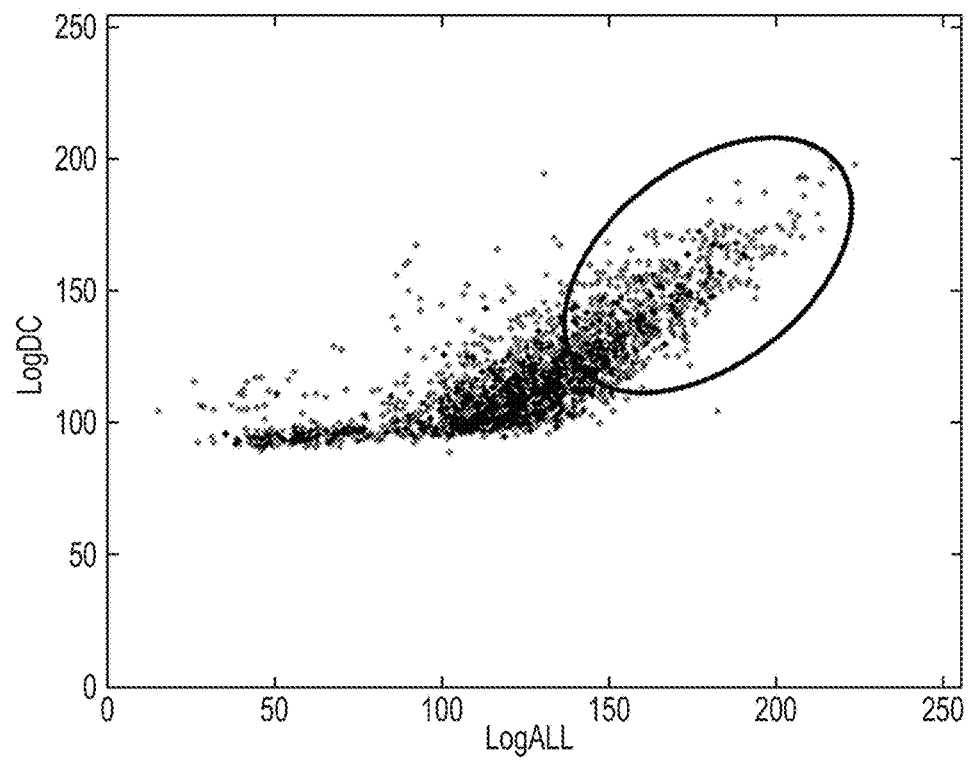
FIG. 17 depicts aspects of a gating technique according to embodiments of the present invention.
Figure 18:
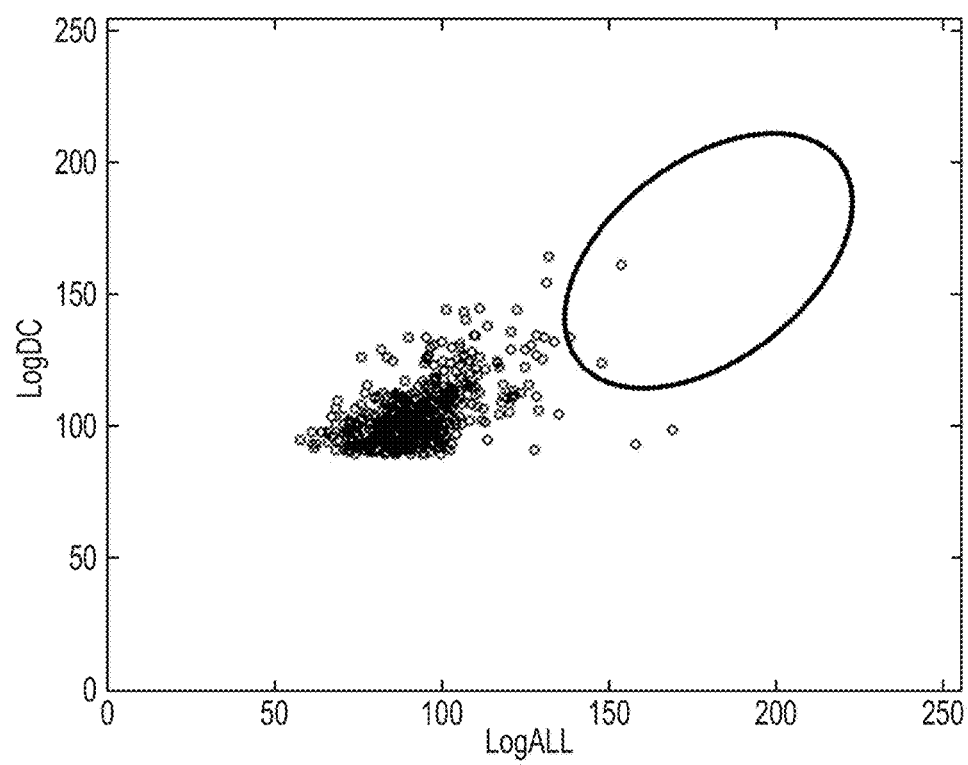
FIG. 18 depicts aspects of a gating technique according to embodiments of the present invention.

In some embodiments the second region (NOT Platelet) can be used to limit or isolate cells or events that are drawn or positioned on the histogram of FIG. 13, such that those isolated cells or events are manifested in the subsequent histogram of FIG. 14. In this way, the use of the region (NOT Platelet) operates as a gating step, by limiting the number of events or cells from the first histogram (of FIG. 13) that are subsequently manifested in the second histogram (of FIG. 14). As a nonlimiting example, the region acts as a gate to filter out or isolate those events within the region boundaries, so that the events are extracted and placed in the next histogram. The term gated as used here means, as a nonlimiting example, that the data present in the histogram is derived using a gating step, as applied to a previous histogram.

Hence, as depicted here, FIG. 14 represents gated data (i.e. gated on NOT Platelet events). In many cases, the parameters of a subsequent histogram are different from those used for the previous histogram. In some cases, a population is isolated using a single gating step. In some cases, a population is isolated using multiple gating steps. As discussed elsewhere here, Boolean logic is in some situations applied to histogram data.

RBC Event Identification

According to some embodiments, RBC events, including both mature RBC's and reticulocytes, can be identified in the EDC vs log ALL view as shown in FIG. 14. The RBC events are located at the lower part of the view, which are enclosed.

Immature Platelet Event Identification

For the purpose of identify immature platelet events, it has been observed that features discussed with regard to such identification can be monotonic. Therefore, if a parameter is used to gate out the immature platelet events, use of linear and logarithmic forms may result in similar outcomes. Hence, in some cases, both forms may be equivalent in terms of gating.

Immature platelets are known to contain intracellular RNA. The non-fluorochrome new methylene blue stain precipitates RNA of the immature platelets and intensifies the light scatters. Therefore, according to some embodiments, primary parameters which can distinguish the immature platelets from mature platelets include light scatters. The Log DC vs (Log Light Scatters) plots of a sample having 19% IPF are shown in FIGS. 15A to 15D, whereas the plots of a sample having almost 0% IPF are shown in FIGS. 16A to 16D. It is clear that there are noticeable immature platelet events in the high-Light-Scatters areas enclosed in FIGS. 15A to 15D, however, the same areas in FIGS. 16A to 16D are almost empty.

In addition to the elevated signal in light scatters, the immature platelets may also exhibit increased volume compared to the mature platelets, which can result in higher DC for the immature platelets. Furthermore, ALL is often considered highly correlated with DC and can also be utilized to gate the immature platelets. For example, FIG. 17 (19% IPF) and FIG. 18 (almost 0% IPF) demonstrate that the immature platelets are located at high DC and high ALL zone.

Accordingly, embodiments of the present invention encompass systems and methods which can separate the immature platelets from the mature platelets based on elevated DC, ALL, LALS, LMALS, MALS, and/or UMALS.

For instance, in certain embodiments, immature platelets can be based on a discriminative parameter as disclosed herein. For example, it is possible to identify immature platelets based on a LogUMALS value which is greater than a threshold (see e.g., FIG. 15D). In certain embodiments, immature platelets can be based on multiple discriminative parameters as disclosed herein. For example, it is possible to identify immature platelets based on a LogUMALS value which is greater than a first threshold and a log DC value which is greater than a second threshold (see e.g., FIG. 15D). Hence, it can be seen that these processing techniques can be used to readily identify and quantify immature platelet populations.

Calculating IP % and IP Count

Given the above identified immature platelets, immature platelet percent (IP %) is calculated as the percentage of the immature platelet with respect to the total platelets.

According to some embodiments, IP % can be calculated as the number of the immature platelet events divided by the number of both mature and immature platelet events (based on counts obtained from Retic module) times 100%, as illustrated in FIG. 7A.

According to some embodiments, IP % can be calculated using both the CBC module and the Reticulocyte module, as illustrated in FIG. 7B, by multiplying the ratio (number of immature platelet events from Retic module)/(number of RBC events from Retic module) by the ratio (RBC count from CBC module)/(total platelet count from CBC module), again multiplied by 100%. The CBC module can produce a reliable total platelet count as well as a reliable RBC count (e.g. RBC#$_{CBC}$), and hence it may be desirable to use the method of FIG. 7B in situations where the mature platelet population may be cut off due to an instrument configuration, or in other instances where it may not be possible or desirable to apply the method illustrated in FIG. 7A.

Similarly, IP % can be calculated using both the CBC module and the Reticulocyte module as illustrated in FIG. 7C. As depicted here, IP % can be calculated by multiplying the ratio (number of immature platelet events from Retic module)/(number of RBC+NRBC+WBC events from Retic module) by the ratio (RBC+NRBC+WBC count from CBC module)/(total platelet count from CBC module), again multiplied by 100%. In some scenarios, the RBC+NRBC+WBC count from the CBC module (e.g. the URBC#$_{CBC}$) can be obtained more reliably than the RBC count, and hence it may be desirable to use an RBC+NRBC+WBC count from the CBC module instead of the RBC count.

In addition to providing techniques for obtaining IP %, embodiments of the present invention encompass systems and methods for obtaining an IP count (number of immature platelets per unit volume) as well. For example, an exemplary IP count can be calculated using the following equation: IP %*(platelet count from CBC module)/100%. The IP % used in determining an IP count can be obtained using any of the approaches disclosed herein.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A hematology system for determining an immature platelet status in a biological sample, the system comprising:
    a volume conductivity scatter (VCS) module that includes (i) an optical element having a cell interrogation zone, (ii) a flow path configured to deliver a hydrodynamically focused stream of the biological sample toward the cell interrogation zone, (iii) a light source oriented to direct a light beam along a beam axis to irradiate cells of the biological sample individually passing through the cell interrogation zone, and (iv) a light detection assembly optically coupled to the cell interrogation zone so as to measure light scattered by and transmitted through the irradiated cells of the biological sample;
    a complete blood count (CBC) module that includes a red blood cell aperture bath configured to determine, based on electrical impedance measurements, a CBC module red blood cell count and a CBC module total platelet count of the biological sample; and
    a data processing module comprising a processor and computer executable code stored on a non-transitory computer readable medium, the computer executable code comprising instructions that when executed on the processor cause the processor to determine (i) a VCS module immature platelet count based on first light measurements from the light detection assembly, the first light measurements comprising a member selected from the group consisting of lower angle light scatter (LALS) measurements, lower median angle light scatter (LMALS) measurements, upper median angle light scatter (UMALS) measurements, and axial light loss (ALL) measurements, (ii) a VCS module red blood cell count based on second light measurements from the light detection assembly, the second light measurements comprising axial light loss (ALL) measurements, and (iii) the immature platelet status based on a multiplication product of a first factor and a second factor, wherein the first factor is a ratio of the CBC module red blood cell count to the CBC module total platelet count and the second factor is the ratio of the VCS module immature platelet count to the VCS module red blood cell count, wherein the immature platelet status comprises an estimation of immature platelet count or an estimation of immature platelet percentage.

2. The system according to claim 1, wherein the first light measurement is the lower angle light scatter (LALS) measurement, and the volume conductivity scatter (VCS) module is configured to determine the immature platelet count when a logLALS value is greater than about 200.

3. The system according to claim 1, wherein the first light measurement is the lower median angle light scatter (LMALS) measurement, and the volume conductivity scatter (VCS) module is configured to determine the immature platelet count when a logLMALS value is greater than about 100.

4. The system according to claim 1, wherein the first light measurement comprises the upper median angle light scatter (UMALS) measurement and the lower median angle light scatter (LMALS) measurement, wherein a median angle light scatter (MALS) is sum of the UMALS and LMALS, and the volume conductivity scatter (VCS) module is configured to determine the immature platelet count when a log MALS value is greater than about 100.

5. The system according to claim 1, wherein the first light measurements comprise the upper median angle light scatter (UMALS) measurements, and the computer executable code comprises instructions that when executed on the processor cause the processor to determine the VCS module immature platelet count when a logUMALS value is greater than about 100.

6. The system according to claim 1, wherein the first light measurement is the axial light loss (ALL) measurement, and the volume conductivity scatter (VCS) module is configured to determine the immature platelet count when a logALL value is greater than about 140.

7. An automated method for determining an immature platelet status in a biological sample, the method comprising:
accessing a data profile concerning the biological sample, the data profile based on assay results obtained from a particle analysis system analyzing the biological sample, the particle analysis system comprising a volume conductivity scatter (VCS) module that includes (i) an optical element having a cell interrogation zone, (ii) a flow path configured to deliver a hydrodynamically focused stream of the biological sample toward the cell interrogation zone, (iii) a light source oriented to direct a light beam along a beam axis to irradiate cells of the biological sample individually passing through the cell interrogation zone, and (iv) a light detection assembly optically coupled to the cell interrogation zone so as to measure light scattered by and transmitted through the irradiated cells of the biological sample, the data profile comprising volume conductivity scatter (VCS) module data for the biological sample obtained from the volume conductivity scatter (VCS) module;
accessing complete blood count (CBC) module data concerning the biological sample, the CBC data comprising a CBC module red blood cell count of the biological sample and a CBC module total platelet count of the biological sample; and
determining the immature platelet status by executing, with a processor, computer executable code stored on a non-transitory computer readable medium, the computer executable code comprising instructions that when executed on the processor cause the processor to determine (i) a VCS module immature platelet count based on first light measurements from the (VCS) module data, the first light measurements comprising a member selected from the group consisting of lower angle light scatter (LALS) measurements, lower median angle light scatter (LMALS) measurements, upper median angle light scatter (UMALS) measurements, and axial light loss (ALL) measurements, (ii) a VCS module red blood cell count based on second light measurements from the (VCS) module data, the second light measurements comprising axial light loss (ALL) measurements, and (iii) the immature platelet status based on a multiplication product of a first factor and a second factor, wherein the first factor is a ratio of the CBC module red blood cell count to the CBC module total platelet count and the second factor is the ratio of a VCS module immature platelet count to a VCS module red blood cell count, wherein the immature platelet status comprises an estimation of immature platelet count or an estimation of immature platelet percentage.

8. The method according to claim 7, further comprising determining a treatment regimen for an individual from whom the biological sample was obtained, based on the immature platelet status.

9. The method according to claim 7, wherein the first light measurement is the lower angle light scatter (LALS) measurement, and the execution of the storage medium comprising the computer application causes the processor to determine the immature platelet count when a logLALS value is greater than about 200.

10. The method according to claim 7, wherein the first light measurement is the lower median angle light scatter (LMALS) measurement, and the execution of the storage medium comprising the computer application causes the processor to determine the immature platelet count when a logLMALS value is greater than about 100.

11. The method according to claim 7, wherein the first light measurement comprises the upper median angle light scatter (UMALS) measurement and the lower median angle light scatter (LMALS) measurement, wherein a median angle light scatter (MALS) is sum of the UMALS and LMALS, and the execution of the storage medium comprising the computer application causes the processor to determine the immature platelet count when a log MALS value is greater than about 100.

12. The method according to claim 7, wherein the first light measurements comprise the upper median angle light scatter (UMALS) measurements, and the execution of the computer executable code causes the processor to determine the immature platelet count event when a logUMALS value is greater than about 100.

13. The method according to claim 7, wherein the first light measurement is the axial light loss (ALL) measurement, and the execution of the storage medium comprising the computer application causes the processor to determine the immature platelet count when a logALL value is greater than about 140.

14. An automated system for estimating an immature platelet status in a biological sample, the system comprising:
(a) a processor; and
(b) a storage medium comprising a computer application that, when executed by the processor, is configured to cause the system to:
   (i) access volume conductivity scatter (VCS) module data concerning the biological sample, the volume conductivity scatter (VCS) module data comprising first light measurements and second light measurements, the first light measurements comprising a member selected from the group consisting of lower angle light scatter (LALS) measurements, lower median angle light scatter (LMALS) measurements, upper median angle light scatter (UMALS) measurements, and axial light loss (ALL) measurements, and the second light measurements comprising axial light loss (ALL) measurements, wherein the volume conductivity scatter (VCS) module data is obtained from a volume conductivity scatter (VCS) module that includes (i) an optical element having a cell interrogation zone, (ii) a flow path configured to deliver a hydrodynamically focused stream of the biological sample toward the cell interrogation zone, (iii) a light source oriented to direct a light beam along a beam axis to irradiate cells of the biological sample individually passing through the cell interrogation zone, and (iv) a light detection assembly optically coupled to the cell interrogation zone so as to measure light scattered by and transmitted through the irradiated cells of the biological sample;
   (ii) access complete blood count (CBC) module data concerning the biological sample, the CBC data comprising a CBC module red blood cell count of the biological sample and a CBC module total platelet count of the biological sample;
   (iii) determine a VCS module immature platelet count based on the first light measurements from the (VCS) module data;
   (iv) determine a VCS module red blood cell count based on the second light measurements;
   (v) estimate the immature platelet status based on a multiplication product of a first factor and a second factor, wherein the first factor is a ratio of the CBC module red blood cell count to the CBC module total platelet count and the second factor is the ratio of the VCS module immature platelet count to the VCS module red blood cell count, wherein the immature platelet status comprises an estimation of immature platelet count or an estimation of immature platelet percentage; and
   (vi) output the immature platelet status from the processor.

15. The system according to claim 14, wherein the processor is configured to receive the volume conductivity scatter (VCS) module data as input.

16. The system according to claim 14, wherein the processor, the storage medium, or both, are incorporated within a hematology machine.

17. The system according to claim 16, wherein the hematology machine generates the volume conductivity scatter (VCS) module data.

18. The system according to claim 14, wherein the processor, the storage medium, or both, are incorporated within a computer, and wherein the computer is in communication with a hematology machine.

19. The system according to claim 14, wherein the hematology machine generates the volume conductivity scatter (VCS) module data.

20. The system according to claim 14, wherein the processor, the storage medium, or both, are incorporated within a computer, and wherein the computer is in remote communication with a hematology machine via a network.

21. The system according to claim 20, wherein the hematology machine generates the volume conductivity scatter (VCS) module data.

* * * * *

UNITED STATES PATENT AND TRADEMARK OFFICE
CERTIFICATE OF CORRECTION

PATENT NO. : 9,939,453 B2
APPLICATION NO. : 14/142369
DATED : April 10, 2018
INVENTOR(S) : Jiuliu Lu et al.

Page 1 of 1

It is certified that error appears in the above-identified patent and that said Letters Patent is hereby corrected as shown below:

In the Claims

Column 34, Line 30 In Claim 19:
Remove "14" and replace with --18--.

Signed and Sealed this
Eighth Day of January, 2019

Andrei Iancu
*Director of the United States Patent and Trademark Office*